United States Patent
Gualfetti et al.

(12)

(10) Patent No.: US 6,623,949 B1
(45) Date of Patent: Sep. 23, 2003

(54) VARIANT EGIII-LIKE CELLULASE COMPOSITIONS

(75) Inventors: Peter Gualfetti, San Francisco, CA (US); Colin Mitchinson, Half Moon Bay, CA (US); Jay Phillips, Palo Alto, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/632,570

(22) Filed: Aug. 4, 2000

(51) Int. Cl.$^7$ .................. C12N 9/42; C12S 11/00; C11D 3/386
(52) U.S. Cl. .................. 435/209; 435/263; 510/392; 241/28; 426/656
(58) Field of Search ................. 435/209, 263; 510/392; 241/28; 426/656

(56) References Cited

FOREIGN PATENT DOCUMENTS

| WO | WO 99/02702 | 1/1999 |
|----|-------------|--------|
| WO | WO 99/31255 | 6/1999 |
| WO | WO 01/47956 | 7/2001 |

OTHER PUBLICATIONS

Accession No. JC2571, 1995.*
Accession No. JU0328, 1993.*
Accession No. P16630, 1990.*
Accession No. 074705, 1998.*
Copy of PCT Search Report PCT/US01/23946, 2002.

* cited by examiner

*Primary Examiner*—Charles L. Patterson, Jr.
(74) *Attorney, Agent, or Firm*—Genencor International, Inc

(57) ABSTRACT

The present invention relates to novel variant EGIII or EGIII-like cellulases that have improved stability. The variant cellulases have performance sensitive residues replaced to a residue having modified stability.

12 Claims, 5 Drawing Sheets

Amino Acid Sequence of Mature EGIII Protein

```
QTSCDQWATFTGNGYTVSNNLWGASAGSGFGCVTAVSLSGGASWHADWQWSGGQNNVKSY  60
QNSQIAIPQKRTVNSISSMPTTASWSYSGSNIRANVAYDLFTAANPNHVTYSGDYELMIW 120
LGKYGDIGPIGSSQGTVNVGGQSWTLYYGYNGAMQVYSFVAQTNTTNYSGDVKNFFNYLR 180
DNKGYNAAGQYVLSYQFGTEPFTGSGTLNVASWTASIN            218
```

FIGURE 1

DNA Sequence of EGIII Without Introns

ATGAAGTTCCTTCAAGTCCTCCCTGCCCTCATACCGGCCGCCCTGG
CCCAAACCAGCTGTGACCAGTGGGCAACCTTCACTGGCAACGGCTA
CACAGTCAGCAACAACCTTTGGGGAGCATCAGCCGGCTCTGGATTT
GGCTGCGTGACGGCGGTATCGCTCAGCGGCGGGGCCTCCTGGCACG
CAGACTGGCAGTGGTCCGGCGGCCAGAACAACGTCAAGTCGTACC
AGAACTCTCAGATTGCCATTCCCCAGAAGAGGACCGTCAACAGCAT
CAGCAGCATGCCCACCACTGCCAGCTGGAGCTACAGCGGGAGCAA
CATCCGCGCTAATGTTGCGTATGACTTGTTCACCGCAGCCAACCCG
AATCATGTCACGTACTCGGGAGACTACGAACTCATGATCTGGCTTG
GCAAATACGGCGATATTGGGCCGATTGGGTCCTCACAGGGAACAG
TCAACGTCGGTGGCCAGAGCTGGACGCTCTACTATGGCTACAACGG
AGCCATGCAAGTCTATTCCTTTGTGGCCCAGACCAACACTACCAAC
TACAGCGGAGATGTCAAGAACTTCTTCAATTATCTCCGAGACAATA
AAGGATACAACGCTGCAGGCCAATATGTTCTTAGCTACCAATTTGG
TACCGAGCCCTTCACGGGCAGTGGAACTCTGAACGTCGCATCCTGG
ACCGCATCTATCAAC

FIGURE 2

```
                                1                                                          60
          T._reesei             M.........KF.LQVLPALIPAALAQTS...............CDQWATFTGNG...YTV
          H._schweinitzii       M.........KF.LQVLPAILPAALAQTS...............CDQYATFSGNG...YIV
          A._aculeatus__*       M.........KAFHL.LAALAGAAVAQQAQ..............LCDQYATYTGGV...YTI
          A._kawachii__*        M.........KLSMT.LSLFAATAMGQT................MCSQYDSASSPP...YSV
          A._kawachii_2         M.........KAFHL.LAALSGAAVAQQAQ.............'.LCDQYATYTGGV...YTI
          A._oryzae__*          M.........KLSLA.LATLVATAFSQE................LCAQYDSASSPP...YSV
          H._grisei             M........LKSALLLGAAAVSVQSASIPTIPANLEPRQIR.SLCELYGYWSGNG...YEL
          H._insolens__*        M.......LKSALLLGPAAVSVQSASIPTIPANLEPRQIR.SLCELYGYWSGNG...YEL
      Chaetomium_brasiliense    M.........KLTLVLFVSSLA......AATPLGWRERQQQVSLCGQSSSWSGNG...YQL
          F._equseti            M.........KSTLLLAGAFAPLAFAKD................LCEQYGYLSSDG...YSL
          F._javanicum_1        M.........KSAIVA.ALAGLAAASPTRLIPRGQ........FCGQWDSETAGA...YTI
          F._javanicum_2        M.........K..FFGVVSASLAATAVATPTTPTETIEKRDTTWCDAFGSLATSG...YTV
          G._roseum_Rj_1        M.........KANIVILSLFAPLAAVAQT...............LCGQYSSNTQGG...YIF
          G._roseum_Rj_2        M.........KSIISFFGLATLVAAAPSQNPTRTQPLEKRATTLCGQWDSVETGG...YTI
          G._roseum_PA_3        M.........KFQLLSLTAFAPLSLAA................LCGQYQSQSQGG...YIF
          G._roseum_Rj_4        M.........KTGIAYLAAVLPLA.MAES...............LCDQYAYLSRDG...YNF
          Memnoniella_echinata  M.........KVAAL.LVALSPLAF.AQS...............LCDQYSYYSSNG...YEF
          Emericella_desertoru  M.........K..LLALSLVSLASAASAASIL.SNTFTRRSD.FCGQWDTATVGN...FIV
          Actinomycete_11AG8    MRS......HPRS..ATM.TVLVVLASLGALLTAAAPAQANQQICDRYGTTTIQD.RYVV
          S._lividans_CelB__*   MRTLRPQARAPRGLLAALGAVLAAFALVSSLVTAAAPAQADTTICEPFGTTTIQG.RYVV
          Rhodothermus_marinus__* MNVMR...AVLVLSLLLLFGCDWL.FPDGDNGKEPEPEPEPTVELCGRWDARDVAGGRYRV
          Erwinia_carot___*     MQTVNTQPHRIFRVLLPAVFSSLLLSSLTVSAASSSNDADKLYF.........GNNKYYL 61                                                         120
          T._reesei             SNNLWGASAGSF..GCV.TAVSLSGG..ASWHADWQWSGGQNNVKSYQNS..........
          H._schweinitzii       SNNLWGASAGSF..GCV.TSVSLNGA..ASWHADWQWSGGQNNVKSYQNV..........
          A._aculeatus__*       NNNLWGKDAGSG..SQCTTVNSASSAG.TSWSTKWNWSGGENSVKSYANS..........
          A._kawachii__*        NQNLWGEYQGTG..SQCVYVDKLSSSG.ASWHTKWTWSGGEGTVKSYSNS..........
          A._kawachii_2         NNNLWGKDAGSG..SQCTTVNSASSAG.TSWSTKWNWSGGENSVKSYANS..........
          A._oryzae__*          NNNLWGQDSGTGFTSQCVYVDNLSSSG.AAWHTTWTWNGGEGSVKSYSNS..........
          H._grisei             LNNLWGKDTATS..GWQCTYLDGTNNGG.IQWSTAWEWQGAPDNVKSYPYV..........
          H._insolens__*        LNNLWGKDTATS..GWQCTYLDGTNNGG.IQWSTAWEWQGAPDNVKSYPYV..........
      Chaetomium_brasiliense    NNNLWGQSRATS..GSQCTYLDSSSNSG.IHWHTTWTWEGGEGEVKSYAYS..........
          F._equseti            NNNVWGKDSGTGD..QCTHVNWNNANG.AGWDVEWNWSGGKDNVKSYPNS..........
          F._javanicum_1        YNNLWGKDNAES..GEQCTTNSGEQSDGSIAWSVEWSWTGGQGQVKSYPNA..........
          F._javanicum_2        YHNNWGKGDATS..GSQCTTFTSVSNNNFV.WSTSWTWAGGAGKVKSYSNV..........
          G._roseum_Rj_1        NNNMWGMGSGSGS..QCTYVDKVWAEG.VAWHTDWSWSGGDNNVKSYPYS..........
          G._roseum_Rj_2        YNNLWGQDNG.S.GSQCLTVEGV.TDGLAAWSSTWSWSGGSSSVKSYSNA..........
          G._roseum_PA_3        NNNKWGQGSGSGS..QCLTIDKTWDSN.VAFHADWSWSGGTNNVKSYPNA..........
          G._roseum_Rj_4        NNNEWGAATGTGD..QCTYVDSTSSGG.VSWHSDWTWSGSESEIKSYPYS..........
          Memnoniella_echinata  NNNMWGRNSGQGN..QCTYVDYSSPNG.VGWRVNWNWSGGDNNVKSYPYS..........
          Emericella_desertoru  YNNLWGQDNADS.GSQ..TGVDSANGNSISWHTTWSWSGGSSSVKSYANA..........
          Actinomycete_11AG8    QNNRWGTSAT.....QCINVT..GNGFEITQADGS..VPTNGAPKSYPSVYDGCHYG...
          S._lividans_CelB__*   QNNRWGSTAP.....QCVTAT..DTGFRVTQADGS..APTNGAPKSYPSVFNGCHYT...
          Rhodothermus_marinus__* INNVWGAETA.....QCIEVGLETGNFTITRADHD..NGNNVA..AYPAIYFGCHWAPAR
          Erwinia_carot___*     FNNVWGKDEIKGWQQTIFYNSPISMG....WN..WHWPSSTHSVKAYPSLVSGWHWTAG.

121                                                        180
          T._reesei             .QIAIP.QKRTVNSISSMPTTASW...SYSGSNIRANVAYDL.FTAANPNHVTYSGDYEL
          H._schweinitzii       .QINIP.QKRTVNSIGSMPTTASW...SYSGSDIRANVAYDL.FTAANPNHVTYSGDYEL
          A._aculeatus__*       .GLTF..NKKLVSQISQIPTTARW.S..YDNTGIRADVAYDL.FTAADINHVTWSGDYEL
          A._kawachii__*        .GLTF..DKKLVSDVSSIPTSVTW.SQD.DTNVQADVSYDL.FTAANADHATSSGDYEL
          A._kawachii_2         .GLSF..NKKLVSQISHIPTAARW.S..YDNTCIRRGRAYDL.FTAADINHVTWSGDYEL
          A._oryzae__*          .AVTF..DKKLVSDVQSIPTDVEW.SQDFTNTNVNADVAYDL.FTAADQNHVTYSGDYEL
          H._grisei             .GKQIQRGRK.ISDINSMRTSVSW...TYDRTDIRANVAYDV.FTARDPDHPNWGGDYEL
          H._insolens__*        .GKQIQRGRK.ISDINSMRTSVSW...TYDRTDIRANVAYDL.FTARDPDHPNWGGDYEL
      Chaetomium_brasiliense    .GRQVSTGLT.IASIDSMQTSVSW...EYNTTDIQANVAYDI.FTAEDPDHEHSSGDYEL
          F._equseti            .ALLIGEDKKTISSITNMQSTAEW...KYSGDNLRADVAYDL.FTAADPNHETSSGEYEL
          F._javanicum_1        .VVEI..EKKTLGEVSSIPSA..W.DWTYTGNGIIANVAYDL.FTSSTESGDA...EYEF
          F._javanicum_2        .ALEK..INKKIDIKSVSTR...W.IWRYTGTKMIANVSYDL.WFAPTASSNN...AYEI
          G._roseum_Rj_1        .GRELGT.KRIVSSIKSISSSGADW...DYTGSNLRANAAYDI.FTSANPNHATSSGDYEV
          G._roseum_Rj_2        .VLSA..EAARISAISSIPSK..W.EWSYTGTDIVANVAYDL.FSNTDCGDTP...EYEI
          G._roseum_PA_3        .GLEFSR.GKKVSSIGTINGGADW...DYSGSNIRANVAYDI.FTSADPNHVTSSGDYEL
          G._roseum_Rj_4        .GLDLPE.KKIVTSIGSISTGAEW...SYSGSDIRADVAYDT.FTAADPNHATSSGDYEV
          Memnoniella_echinata  .GRQLPT.KRIVSWIGSLPTTVSW...NYQGNNLRANVAYDL.FTAANPNHPNSSGDYEL
          Emericella_desertoru  .AYQF..TSTKLNSLSSIPTS...W.KWQYSTTDIVANVAYDL.FTSSSAGGDS...EYEI
```

FIGURE 3A

```
         Actinomycete_11AG8  ...NCAPRTTLPMRISSIGSAPSSVSYRYTGNGVY.NAAYDIWLDPTPRTNGVNR..TEI
          S._lividans_CelB * ...NCSPGTDLPVRLDTVSAAPSSISYGFVDGAVY.NASYDIWLDPTARTDGVNQ..TEI
       Rhodothermus_marinus* AIRDCAARAGAVRRAHELDVTP.......ITTGRW.NAAYDIWFSPVTNSGNGYSGGAEL
             Erwinia_carot* ....YTENSGLPIQLSSNKSITSNVTYSIKATGTY.NAAYDIWFHTTDKANWDSSPTDEL 181                                                        240
                  T._reesei  MIWLGKYGDIGPIGSS....QGTVNVGGQSWTLYYGYNGAMQV......YSFVAQT.NTT
             H._schweinitzii MIWLGKYGDIGPIGSS....QGTVNVGGQTWTLYYGYNGAMQV......YSFVAQS.NTT
               A._aculeatus* MIWLARYGGVQPIGSQ....IATATVDGQTWELWYG......ANGSQKTYSFVAPT.PIT
               A._kawachii * MIWLARYGSVQPIGKQ....IATATVGGKSWEVW..YGTSTQAGAEQKTYSFVAGS.PIN
              A._kawachii_2  MIWLARYGGVQPLGSQ....IATATVEGQTWELWYG......VNGAQKTYSFVAAN.PIT
                A._oryzae *  MIWLARYGTIQPIGTQ....IDTATVEGHTWELWFTYGTTIQAGAEQKTYSFVSAT.PIN
                  H._grisei  MIWLARYGGIYPIGTF....HSQVNLAGRTWDLWTGYNGNMRV......YSFLPPSGDIR
              H._insolens *  MIWLARYGGIYPIGTF....HSQVNLAGRTWDLWTGYNGNMRV......YSFLPPSGDIR
         Chaetomium_brasiliense MIWLARYNNVSPIGSS....VATATVGGDTWDLFAGANGDMEV......YSFVAENT.MN
                 F._equseti  MVWLARIGGVQPIGSL....QTSVTIEGHTWELWVGMNGSMKV......FSFVAPT.PVN
              F._javanicum_1 MIWLSALGGAGPISNDGSP.VATAELAGTSWKLYQGKNNQMTV......FSFVAESDV.N
              F._javanicum_2 MIWVGAYGGALPISTPGKGVIDRPTLAGIPWDVYKGPNGDVTV......ISFVASSNQ.G
                G._roseum_Rj_1 MIWLANLGGLTPIGSP....IGTVKAAGRDWELWDGYNGAMRV......YSFVAPS.QLN
                G._roseum_Rj_2 MIWLSALGGAGPISSTGSS.IATVTIAGASWNLWQGQNNQMAV......FSFVAESDQ.K
                G._roseum_PA_3 MIWLGKLGDIYPIGNS....IGRVKAANREWDLHVGYNGAMKV......FSFVAPS.PVT
                G._roseum_Rj_4 MIWLANLGGLTPIGSP....IGTVKAAGRDWELWDGYNGAMRV......YSFVAPS.QLN
          Memnoniella_echinata MIWGRLGNVYPIGNQ....VATVNIAGQQWNLYYGYNGAMQV......YSFVSPN.QLN
          Emericella_desertoru MIWLAALGGAGPISSTGSS.IATVTLGGVTWSLYSGPNGSMQV......YSFVASSTT.E
         Actinomycete_11AG8  MIWFNRVGPVQPIGSP....VGTAHVGGRSWEVWTGSNGSNDVI......SFLAPSA.IS
          S._lividans_CelB * MIWFNRVGPIQPIGSP....VGTASVGGRTWEVWSGGNGSNDVL......SFVAPSA.IS
       Rhodothermus_marinus* MIWLNWNGGVMPGGSR....VATVELAGATWEVWYADWDWNYIA......YRRTTPT.TS
             Erwinia_carot*  MIWLNDTNA.....GPAGDYIETVFLGDSSWNVFKGWINADN.GGGWNVFSFVHTSGTNS 241                                                        300
                  T._reesei  NYSGDVKNFFNYLRDNKGYNAAGQYV..LSYQFGTEPF..TGSGT.LNVASWTASI.N..
             H._schweinitzii SYSGDVKNFFNYLRDNKGYNAGGQYV..LSYQFGTEPF..TGSGT.LNVASWTASI.N..
               A._aculeatus* SFQGDVNDFFKYLTQNHGFPASSQYLI..TLQFGTEPF..TGGPATLSVSNWSASVQQAG
               A._kawachii * SWSGDIKDFFNYLTQNQGFPASSQHLI..TLQCGTEPF..TGGPATFTVDNWTASVN...
              A._kawachii_2  SFQGDINDFFKYLTQNHGFPASSQYLIILALQFGTEPF..TGGPATLNVADWSASVQ...
                A._oryzae *  TFGGDIKFFDYITSKHSFPASAQYLI..NMQFGTEPFFTTGGPVTFTVPNWTASVN...
                  H._grisei  DFSCDIKDFFNYLERNHGYPAREQNLIV..YQVGTECF..TGGPARFTCRDFRADL....
              H._insolens *  DFSCDIKDFFNYLERNHGYPAREQNLIV..YQVGTECF..TGGPARFTCRDFRADL....
         Chaetomium_brasiliense SFSGDVKDFFDYLEQNVGFPVDDQYLLV..FELGSEAF..TGGPATLSVSQFSANI....
                 F._equseti  NFNADIKQFWDYLTKSQNFPADNQYL..LTFQFGTEPF..TGDNAKFTVTNFNAHLK...
              F._javanicum_1 NFCGDLADFTDYLVDNHGVSSSQ...ILQSVGAGTEPF..EGTNAVFTTNNYHADVE...
              F._javanicum_2 NFQADLKEFLNYLTSKQGLPSNY...VATSFQAGTEPF..EGTNAVLKTSAYTISVN...
                G._roseum_Rj_1 SFDGEIMDFFYVVKDMRGFPADSQHL..LTVQFGTEPI..SGSGAKFSVSHWSAKLG...
                G._roseum_Rj_2 SFSGDLNDFIQYLVDSQGYSGSQ...CLYSIGAGTEPF..TGTDAEFITTGYSVSVSAGD
                G._roseum_PA_3 RFDGNIMDFFYVMRDMQGYPMDKQYL..LSLQFGTEPF..TGSNAKFSCWYFGAKIK...
                G._roseum_Rj_4 SFDGEIMDFFYVVKDMRGFPADSQHL..LTVQFGTEPI..SGSGAKFSVSHWSAKLG...
          Memnoniella_echinata YFSGNVKDFFTYLQYNRAYPADSQYL..ITYQFGTEPF..TGQNAVFTVSNWSAQQNN..
          Emericella_desertoru SFSADLMDFINYLAENQGLSSSQ...YLTHVQAGTEPF..TGTDATLTVSSYSVSVS...
         Actinomycete_11AG8  SWSFDVKDFVD.QAVSHGLATPDWYLT..SIQAGFEPW...EGGTGLAVNFSSAVNAG.
          S._lividans_CelB * GWSFDVMDFVR.ATVARGLAENDWYLT..SVQAGFEPW...QNGAGLAVNSFSSTVETGT
       Rhodothermus_marinus* VSELDLKAFID.DAVARGYIRPEWYLH..AVETGFELW...EGGAGLRTADFSVTVQ...
             Erwinia_carot*  A.SLNIRHFTDYLVQTKQWMSDEKYIS..SVEFGTEIF...GGDGQIDITEWRVDVK...

301                                                        360
                  T._reesei  ............................................................
             H._schweinitzii ............................................................
               A._aculeatus* F.......................................EPWQNGAGLAVNSF....
               A._kawachii * ............................................................
              A._kawachii_2  ............................................................
                A._oryzae *  ............................................................
                  H._grisei  .......................................W..................
              H._insolens *  .......................................W..................
         Chaetomium_brasiliense .......................................A..................
                 F._equseti  ............................................................
              F._javanicum_1 ............................................................
              F._javanicum_2 ............................................................
                G._roseum_Rj_1 ............................................................
                G._roseum_Rj_2 SGCDETTTSSQAQSSTVETSTATQPQS...SSTVVPTVTLS.QPSNESTTTPVQSQ....
                G._roseum_PA_3 ............................................................
                G._roseum_Rj_4 ............................................................
          Memnoniella_echinata ............................................................
          Emericella_desertoru ............................................................
         Actinomycete_11AG8  ..GGNGGTPGTPAACQVSYSTHTWPGGFTVDTTITNTGSTPVDGWELDFTLPAGHTVTSA
          S._lividans_CelB * PGGTDPGDPGGPSACAVSYGTNVWQDGFTADVTVTNTGTAPVDGWQLAFTLPSGQRITNA
       Rhodothermus_marinus* ............................................................
```

FIGURE 3B

```
                     Erwinia_carot___*    ............................................................
                                          361
          419
                           T._reesei      ............................................................
                     H._schweinitzii      ............................................................
                     A._aculeatus__*      ......SSTV..................................................
                      A._kawachii__*      ............................................................
                       A._kawachii_2      ............................................................
                        A._oryzae__*      ............................................................
                           H._grisei      ............................................................
                       H._insolens__*     ............................................................
                Chaetomium_brasiliense    ............................................................
                          F._equseti      ............................................................
                       F._javanicum_1     ...........................................................Y
                       F._javanicum_2     ............................................................
                        G._roseum_Rj_1    ............................................................
                        G._roseum_Rj_2    ......PSSVETTPTAQPQSSSVQTTTTAQA....QPTSGTGCSRRRKRR......AVV
                        G._roseum_PA_3    ............................................................
                        G._roseum_Rj_4    ............................................................
                    Memnoniella_echinata  ............................................................
                    Emericella_desertoru  ............................................................
                     Actinomycete_11AG8   WNALISPASGAVTARSTGSNGRIAANGGTQSFGFQGTSSGTGFNAPAGGRLNGTSCTVR
                     S._lividans_CelB__*  WNASLTPSSGSVTATGASHNARIAP.GGSLSFGFQGTYGGA.FAEPTGFRLNGTACTTV
                  Rhodothermus_marinus__* ............................................................
                     Erwinia_carot___*    ............................................................
```

FIGURE 3C

VARIANT EGIII-LIKE CELLULASE COMPOSITIONS

CROSS-REFERENCE TO RELATED APPLICATIONS

This Application is related to concurrently filed applications with Ser. Nos. 09/632,575, 09/633,084, 09/632,426 and 09/633,085, all filed on Aug. 4, 2000, all of which are incorporated by reference in their entirety.

GOVERNMENT-SPONSORED RESEARCH AND DEVELOPMENT

Not applicable.

BACKGROUND OF THE INVENTION

Cellulases are enzymes which are capable of hydrolysis of the β-D-glucosidic linkages in celluloses. Cellulolytic enzymes have been traditionally divided into three major classes: endoglucanases, exoglucanases or cellobiohydrolases and β-glucosidases (Knowles, J. et al., (1987), *TIBTECH* 5, 255–261); and are known to be produced by a large number of bacteria, yeasts and fungi.

Although cellulases are used to degrade wood pulp and animal feed, cellulases are primarily used in the treatment of textiles, e.g., in detergent compositions for assisting in the removal of dirt or grayish cast (see e.g., Great Britain Application Nos. 2,075,028, 2,095,275 and 2,094,826) or in the treatment of textiles prior to sale to improve the feel and appearance of the textile. Thus, Great Britain Application No. 1,358,599 illustrates the use of cellulase in detergents to reduce the harshness of cotton containing fabrics.

Cellulases have also been used in the treatment of textiles to recondition used fabrics by making their colors more vibrant (see e.g., The Shizuoka Prefectural Hammamatsu Textile Industrial Research Institute Report, Vol. 24, pp. 54–61 (1986)). Repeated washing of cotton containing fabrics results in a grayish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

Because of its effectiveness in many industrial processes, there has been a trend in the field to search for specific cellulase compositions or components which have particularly effective performance profiles with respect to one or more specific applications. As possible sources of cellulases, practitioners have focused on fungi and bacteria. For example, cellulase produced by certain fungi such as Trichoderma spp. (especially *Trichoderma reesei*) have been given much attention because a complete cellulase system capable of degrading crystalline forms of cellulose is readily produced in large quantities via fermentation procedures. This specific cellulase complex has been extensively analyzed to determine the nature of its specific components and the ability of those components to perform in industrial processes (see, Wood et al., "Methods in Enzymology", 160, 25, pages 234, et seq. (1988). U.S. Pat. No. 5,475,101 (Ward et al.) discloses the purification and molecular cloning of one particularly useful enzyme called endoglucanase III (EGIII) which is derived from *Trichoderma reesei*.

PCT Publication No. WO 94/14953 discloses endoglucanases which are encoded by a nucleic acid which comprises any one of a series of DNA sequences, each having 20 nucleotides.

Ooi, et al., *Curr. Genet.* 18:217–222 (1990) disclose the cDNA sequence coding for endoglucanase F1-CMC produced by *Aspergillus aculeatus* which contains the amino acid strings NNLWG, ELMIW and GTEPFT. Sakamoto, et al., *Curr. Genet.* 27:435–439 (1995) discloses the cDNA sequence encoding the endoglucanase CMCase-1 From *Aspergillus kawachii* IFO 4308 which contains the amino acid strings ELMIW and GTEPFT. Ward, et al., discloses the sequence of EGIII having the amino acid strings NNLWG, ELMIW and GTEPFT. Additionally, two cellulase sequences, one from *Erwinia carotovara* and *Rhodothermus marinus* are disclosed in Saarilahti, et al., *Gene* 90:9–14 (1990) and Hreggvidsson, et al., *Appl. Environ. Microb.* 62:3047–3049 (1996) which contain the amino acid string ELMIW.

Despite knowledge in the art related to many cellulase compositions having applications in some or all of the above areas, there is a continued need for new cellulase compositions which have improved stability under conditions present in applications for which cellulases are useful, e.g., household and laundry detergents and textile treatment compositions.

SUMMARY OF THE INVENTION

According to the present invention, a variant EGIII or EGIII-like cellulase is provided wherein one or more amino acids are modified or deleted to confer improved performance, including stability in the presence of thermal and/or surfactant mediated stress. In another embodiment of the invention, residues critical for the stability of an EGIII-like cellulase are identified.

In a preferred embodiment, a variant EGIII or EGIII-like cellulase is provided, wherein the variant comprises a substitution or deletion at a position corresponding to one or more of residues P201, G170 and/or V210 in EGIII from *Trichoderma reesei*.

In a more preferred embodiment of this aspect of the invention, the variant comprises a substitution at a position corresponding to one or more of residues P201C, G170C and/or V210C in EGIII.

In an alternative embodiment, the EGIII-like cellulase of this invention, comprises a substitution at a position corresponding to one or more of residues C190G/S, C221S/P and or C231S/V of *H grisea*.

In a different aspect of this embodiment, the EGIII-like cellulase is derived from a fungus, bacteria or Actinomycete. In a preferred aspect, the cellulase is derived from a fungus. In a more preferred aspect, the filamentous fungus. In a most preferred aspect, the filamentous fungus belongs to Euascomycete, in particular Aspergillus spp., Gliocladium spp., Fusarium spp., Acremonium spp., Myceliophtora spp., Verticillium spp., Myrothecium spp., or Penicillium spp.

In another embodiment, the EGIII-like cellulase of this invention is an endoglucanase.

In yet another embodiment of this invention, a DNA that encodes an EGIII-like cellulase is provided. In one aspect of this embodiment, the DNA is on a vector. In another aspect of this embodiment, the DNA is in a host cell transformed with the vector.

In a further embodiment, a method for producing an EGIII-like cellulase of this invention is provided. Specifically, a method is provided comprising the steps of culturing a host cell in a suitable culture medium under suitable conditions to produce cellulase, and obtaining said produced cellulase.

In yet another embodiment, a detergent composition is provided that comprises a surfactant and a variant EGIII-like cellulase comprising a substitution or deletion at a position corresponding to one or more of residues P201, G170 and/or V210 in EGIII from *Trichoderma reesei*. In a preferred aspect of this embodiment, the variant comprises a substitution at a position corresponding to one or more of residues P201C, G170C and/or V210C in EGIII. In another aspect of this embodiment, the detergent is a laundry detergent. In yet another aspect, the detergent is a dish detergent.

As shown in more detail below, the substitutions identified herein are important to the stability of EGIII and EGIII-like enzymes, particularly under thermal stress. Accordingly it is within the scope of the present invention to use the EGIII or EGIII-like enzyme in textile treatment, e.g., in laundry detergent or stone washing compositions, in the reduction of biomass, in the production of feed additives or treatment of feed, in the treatment of wood pulp for the production of paper or pulp based products, and in the treatment of starch during grain wet milling or dry milling to facilitate the production of glucose, high fructose corn syrup and/or alcohol.

BRIEF DESCRIPTION OF THE DRAWINGS

FIG. 1 illustrates the amino acid sequence of mature EGIII protein from *Trichoderma reesei* (SEQ ID NO:1) showing the residues described in accordance with the present invention.

FIG. 2 illustrates the DNA sequence of EGIII from *Trichoderma reesei* without introns (SEQ ID NO:2).

FIG. 3 illustrates an alignment of the full length sequence of 20 EGIII-like cellulases in alignment with EGIII, indicating equivalent residues based on primary sequence modeling, including those derived from *Trichoderma reesei* (SEQ ID NO:3), *Hypocrea schweinitzii* (SEQ ID NO:4), *Aspergillus aculeatus* (SEQ ID NO:5), *Aspergillus kawachii* (1) (SEQ ID NO:6) *Aspergillus kawachii* (2) (SEQ ID NO:7), *Aspergillus oryzae* (SEQ ID NO:8), *Humicola grisea* (SEQ ID NO:9), *Humicola insolens* (SEQ ID NO:10), *Chaetomium brasilliense* (SEQ ID NO:11), *Fusarium equiseti* (SEQ ID NO:12), *Fusarium javanicum* (1) (SEQ ID NO:13), *Fusarium javanicum* (2) (SEQ ID NO:14), *Gliocladium roseum* (1) (SEQ ID NO:15), *Gliocladium roseum* (2) (SEQ ID NO:16), *Gliocladium roseum* (3) (SEQ ID NO:17), *Gliocladium roseum* (4) (SEQ ID NO:18), *Memnoniella echinata* (SEQ ID NO:19), *Emericella desertoru* (SEQ ID NO:20), Actinomrycete 11AG8 (SEQ ID NO:21), *Streptomryces lividans* CelB (SEQ ID NO:22), *Rhodothermus marinus* (SEQ ID NO:23), and *Erwinia carotovara* (SEQ ID NO:24).

DETAILED DESCRIPTION OF THE INVENTION

Applicants have isolated novel members of a family of cellulases that have homology to EGIII from *Trichoderma reesei*. Analysis of these cellulases has resulted in differential performance between the cellulases, despite significant homology. In particular, it was discovered that the EGIII-like cellulases from *Humicola grisea* have superior performance under conditions of thermal stress. By aligning the amino acid sequences in these EGIII-like cellulases with that of EGIII, it is possible to identify residue differences between the thermally more stable cellulases and EGIII, thus identifying residues which are important for the improved thermal stability of EGIII-like cellulases. Accordingly, by optimizing the identified residues in EGIII as well as in the EGIII-like cellulases, it is possible to further improve the thermal stability of both the EGIII and the EGIII-like cellulases. Conversely, by recruiting residues critical for stability from a less stable enzyme, the thermal stability of an EGIII-like cellulase can be reduced.

The present invention thus encompasses all such modifications that are identified through the amino acid sequence comparison of EGIII-like cellulases. Particular attention is made to those modifications that result in a change of enzyme thermal stability.

In a preferred embodiment, cysteines present in a *H. grisea* EGIII-like cellulase are recruited into EGIII from *T. reesei*. In a most preferred embodiment, cysteines are substituted at positions 170, 201 and 210 of mature *T. reesei*.

The improved protein according to the present invention comprises an amino acid sequence that is derived from the amino acid sequence of a precursor protein. The precursor protein may be a naturally occurring protein or a recombinant protein. The amino acid sequence of the improved protein is derived from the precursor protein's amino acid sequence by the substitution, deletion or insertion of one or more amino acids of the precursor amino acid sequence. Such modification is generally of the precursor DNA sequence that encodes the amino acid sequence of the precursor proteins rather than manipulation of the precursor protein per se. Suitable methods for such manipulation of the precursor DNA sequence include methods disclosed herein and in commonly owned U.S. Pat. Nos. 4,760,025 and 5,185,258, incorporated herein by reference.

Sequence alignments may be produced using different EGIII-like cellulases and may slightly differ from one alignment to another depending on the number of sequences and the degree of homology. Suitable experiments to determine appropriate modifications are routine to the ordinarily skilled worker in conjunction with the present disclosure.

Within the specification, certain terms are disclosed which are defined below so as to clarify the nature of the claimed invention.

"Cellulase" is a well-classified category of enzymes in the art and includes enzymes capable of hydrolyzing cellulose polymers to shorter cellooligosaccharide oligomers, cellobiose and/or glucose. Common examples of cellulase enzymes include exo-cellobiohydrolases and endoglucanases and are obtainable from many species of cellulolytic organisms, particularly including fungi and bacteria.

"EGIII" cellulase refers to the endoglucanase component described in Ward et al., U.S. Pat. No. 5,475,101 and Proceedings on the Second TRICEL Symposium on *Trichoderma reesei* Cellulases And Other Hydrolases, Suominen & Reinikainen eds., Espoo Finland (1993), pp. 153–158 (Foundation for Biotechnical and Industrial Fermentation Research, Vol. 8). As discussed therein, EGIII is derived from *Trichoderma reesei* and is characterized by a pH optimum of about 5.8, an isoelectric point (pI) of about 7.4 and a molecular weight of about 25 kD. The enzyme commonly referred to as EGII from *Trichoderma reesei* has been previously referred to in the literature by the nomenclature EGIII by some authors, but that enzyme differs substantially from the enzyme defined herein as EGIII in terms of molecular weight, pI and pH optimum.

"EG-III like enzyme", "EGIII-like protein" or "EGIII-like cellulase" according to the present invention means enzymes that are related to EGIII by having certain amino acid strings in common with EGIII. As used herein, EGIII-like cellulase is also intended to encompass EGIII from *Trichoderma reesei*. Thus an EGIII-like cellulase comprises an enzyme having cellulolytic activity which comprises an amino acid sequence comprising therein an amino acid string selected from the group consisting of one or more of:

1) Asn-Asn-(Leu/Phe/Lys/Ile)-Trp-Gly (SEQ ID NO:25)
2) Glu-(Leu/Phe/Ile)-Met-Ile-Trp (SEQ ID NO:26)
3) Gly-Thr-Glu-Pro-Phe-Thr; (SEQ ID NO:27)
4) (Ser/Tyr/Cys/Trp/Thr/Asn/Lys/Arg)-(Val/Pro)-(Lys/Ala)-(Ser/Ala)-(Tyr/Phe); and (SEQ ID NO:28)
5) Lys-Asn-Phe-Phe-Asn-Tyr. (SEQ ID NO:29)

In one embodiment, the enzyme of the invention further has significant structural and/or sequence homology to EGIII. Thus, in one aspect of this embodiment of the invention, the enzyme has at least 30%, preferably at least 40% and most preferably at least 60% amino acid identity to EGIII. However, it should be recognized that homology alone is often not an appropriate measure for whether a particular enzyme identified by the methods described herein represents an EGIII-like enzyme. Similar enzymatic function with or without reduced homology may identify an EGIII-like cellulase. Accordingly, while homologous enzymes are indeed detected by the methods described and exemplified herein, the degree of homology should not be seen as limiting the scope of the invention.

It is contemplated the EGIII-like cellulases of the invention may be found in many organisms which produce cellulases. However, likely sources of EGIII-like cellulase include those derived from a bacterium or fungus, and more particularly, from an Actinomycete, a Bacillus or a filamentous fungus. In a preferred embodiment, the cellulase is derived from the filamentous fungal family Metazoa, preferably Euascomycetes. Within Metazoa, fungal phylogenetic classifications that produce EGIII-like cellulases include the mitosporic Pyrenomycetes (including Acremonium), Sordariales (including Thielavia), Hypocreales (including Nectriaceae such as Fusarium, Necitia, Verticillium, Myrothecium and Gliocladium; and Hypocrea) and Eurotiales (including mitosporic Trichocomaceae such as Aspergillus and Penicillium).

The Euascomycete preferably belongs to Diaporthales, Halosphaeriales, Microascales, Ophiostomatales, Phyllachorales, Sordariales or Xylariales. Also preferably, the Eusacomycete belongs to Hypocreales comprising Clavicipitaceae, Melanosporaceae, Nectriaceae, Niessliaceae or Mitosporic Hypocreales. Further preferably, the Euascomycete belongs to Hypocreaceae, wherein said Hypocreaceae does not comprise Trichoderma. Most preferably, the Euascomycete is Gliocladium spp., Fusarium spp., Acremonium spp., Myceliophtora spp., Verticillium spp., Myrothecium spp., Penicillium spp., Chaetomium spp., Emercella spp., and Phanerochaete spp. Specific organisms which are contemplated as possessing EGIII-like cellulases include *Chaetomium thermophilum* var. therm., *Chaetomium atrobrunneum, Chaetomium brasiliense, Chaetomium globosum, Chaetomium vitellium, Paecilomyces lilacinus, Chaetomium thermophilum* var. dissitum, *Humicola insolens, Humicola brevis, Memnoniella echinata, Fusarium equiseti, Fusarium oxysporum, fusarium stilboides, Myceliophthora thermophila, Fusarium javanicum, Humicola grisea* var. thermoidea, *Stibella thermophila, Melanocarpus albomyces, Arthrobotrys superba, Myceliophthora hinunilea, Chaetomium pachypodiodes, Myrothecium verrucaria, Penicillium crysogenum, Malbranchea sulfurea, Lunulospora curvula, Emericella desertorum, Acremonium strictum, Cylindrocarpon heteronema,* and *Ulocladium chartarum*. Within the Actinomycetes, Streptomyces appears to possess EGIII-like cellulases.

EGIII-like cellulases according to the invention may be obtained according to the following methods. Degenerate DNA primers are constructed which encode an amino acid sequence selected from the group consisting of one or more of:

1) Asn-Asn-(Leu/Phe/Lys/Ile)-Trp-Gly (SEQ ID NO:25)
2) Glu-(Leu/Phe/Ile)-Met-Ile-Trp (SEQ ID NO:26)
3) Gly-Thr-Glu-Pro-Phe-Thr (SEQ ID NO:27);
4) (Ser/Tyr/Cys/Trp/Thr/Asn/Lys/Arg)-(Val/Pro)-(Lys/Ala)-(Ser/Ala)-(Tyr/Phe) (SEQ ID NO:28); and
5) Lys-Asn-Phe-Phe-Asn-Tyr (SEQ ID NO:29)

and used to clone DNA, and genes, encoding enzymes having cellulolytic activity according to established methods. Techniques for obtaining DNA using degenerate primers are well known in the art and can be found in Sambrook et al. *Molecular Cloning—A Laboratory Manual* (2ND ED.) VOL. 1–3, Cold Springs Harbor Publishing (1989) ("Sambrook"); and *Current Protocols in Molecular Biology*, Ausubel et al. (eds.), Current Protocols, a joint venture between Greene Publishing Associates, Inc. and John Wiley & Sons, Inc., (1997 Supplement) ("Ausubel"). In addition, the EGIII of the invention may be obtained by other methods conventional in molecular biology, e.g., library screening with labeled probes, expression screening and PCR cloning, using one of the cellulase backbones identified herein as an EGIII-like cellulase.

The degenerate primers can be used as hybridization probes against a genomic library obtained from a target organism to analyze whether a given fragment correlates to a similar sequence in the target organism. A useful hybridization assay is as follows: Genomic DNA from a particular target source is fragmented by digestion with a restriction enzyme(s), e.g., EcoR I, Hind III, Bam HI, Cla I, Kpn I, Mlu I, Spe I, Bgl II, Nco I, Xba I, Xho I and Xma I (supplied by New England Biolabs, Inc., Beverly, Mass. and Boehringer Mannheim) according to the manufacturer's instructions. The samples are then electrophoresed through an agarose gel (such as, for example, 0.7% agarose) so that separation of DNA fragments can be visualized by size. The gel may be briefly rinsed in distilled $H_2O$ and subsequently depurinated in an appropriate solution (such as, for example, 0.25M HCl) with gentle shaking followed by denaturation for 30 minutes (in, for example, 0.4 M NaOH). A renaturation step may be included in which the gel is placed in 1.5 M NaCl, IM Tris, pH 7.0 with gentle shaking for 30 minutes. The DNA is then be transferred onto an appropriate positively charged membrane, for example the Maximum Strength Nytran Plus membrane (Schleicher & Schuell, Keene, N.H.), using a transfer solution (such as, for example, 6×SSC (900 mM NaCl, 90 mM trisodium citrate). After the transfer is complete, generally at about 2 hours or greater, the membrane is rinsed (in, for example, 2×SSC[2×SSC=300 mM NaCl, 30 mM trisodium citrate]) and air dried at room temperature. The membrane is then be prehybridized, (for approximately 2 hours or more) in a suitable prehybridization solution (such as, for example, an aqueous solution containing per 100 mL: 30–50 mL formamide, 25 mL of 20×SSPE (1×SSPE=0.18 M NaCl, 1 mM EDTA, 10 mM $NaH_2PO_4$, pH 7.7), 2.5 mL of 20% SDS, and 1 mL of 10 mg/ml sheared herring sperm DNA).

A DNA probe corresponding to the primer sequences above is be isolated by electrophoresis in an agarose gel, the fragment excised from the gel and recovered from the excised agarose. This purified fragment of DNA is then labeled (using, for example, the Megaprime labeling system according to the instructions of the manufacturer to incorporate $P^{32}$ in the DNA (Amersham International PLC, Buckinghamshire, England)). The labeled probe is denatured by heating to 95° C. for 5 minutes and immediately added to the prehybridization solution above containing the membrane. The hybridization reaction should proceed for an appropriate time and under appropriate conditions, for example, 18 hours at 37° C. with gentle shaking. The membrane is rinsed (for example, in 2×SSC/0.3% SDS) and then washed with an appropriate wash solution and with gentle agitation. The stringency desired will be a reflection of the conditions under which the membrane (filter) is washed.

Specifically, the stringency of a given reaction (i.e., the degree of homology necessary for successful hybridization) will largely depend on the washing conditions to which the filter from the Southern blot is subjected after hybridization. "Low-stringency" conditions as defined herein will comprise washing a filter from a Southern blot with a solution of 0.2×SSC/0.1% SDS at 20° C. for 15 minutes. Standard-stringency conditions comprise a further washing step comprising washing the filter from the Southern blot a second time with a solution of 0.2×SSC/0.1% SDS at 37° C. for 30 minutes.

In a preferred embodiment according to this aspect of the invention, degenerate primers are prepared corresponding to one or more of the above peptides. The primers are combined with a genomic DNA from a target organism (i.e., the organism in which the EGIII-like cellulase is sought) under conditions suitable to initiate a standard PCR reaction. In this embodiment, it is advantageous to select degenerate primers corresponding to peptides (a) and/or (d) plus primers corresponding to (c) and/or (e) and amplify DNA with those primers. After the PCR reaction has been performed, the resulting DNA is run on a polyacrylamide gel and bands corresponding in size to the EGIII fragment comprising peptides (a) and/or (d) in addition to (c) and/or (e), i.e., those in the 400–1000 base pair range, are selected. These fragments are pooled and reamplified using primers corresponding to peptides (a) and/or (d) plus primers corresponding to peptide (b) or, alternatively, using primers corresponding to peptide (c) and/or (e) plus primers corresponding to peptide (b). Strong bands of the expected size (in the case of EGIII-like cellulases, the bands will correspond to approximately 250–500 base pair) are excised and sequenced. The isolated sequences are then used to design primers and these primers are used via, e.g., rapid amplification of genomic DNA ends (RAGE), to obtain the full length gene, see e.g., Mizobuchi, et al., *BioTechniques* 15:215–216 (1993).

The DNA that hybridizes with the DNA primers outlined above and thus identified by this method a corresponding EGIII encoding gene may be isolated by routine methods and used to express the corresponding EGIII-like cellulase according to routine techniques. Upon obtaining the cloned gene, routine methods for insertion of the DNA into a vector that can then be transformed into a suitable host cell are used. Culturing the transformed host cell under appropriate conditions results in production of the EGIII-like cellulase that can be obtained, purified and prepared as necessary for a particular application.

The EGIII-like cellulases of the invention are preferably isolated or purified. In the context of the present invention, purification or isolation generally means that the EGIII-like cellulase is altered from its natural state by virtue of separating the EGIII-like cellulase from some or all of the naturally occurring substituents with which it is associated in nature, e.g., the source organism or other cellulases or enzymes expressed by the source organism in conjunction with the EGIII cellulase. Similarly, the EGIII-like cellulases of the invention may be combined with other components that are not naturally present in the natural state. Isolation or purification may be accomplished by art recognized separation techniques such as ion exchange chromatography, affinity chromatography, hydrophobic separation, dialysis, protease treatment, ammonium sulfate precipitation or other protein salt precipitation techniques, centrifugation, size exclusion chromatography, filtration, microfiltration, gel electrophoresis or separation on a gradient to remove whole cells, cell debris, impurities, extraneous proteins, or enzymes undesired in the final composition.

A residue in an EGIII-like cellulase which is "corresponding" or "equivalent" to a residue present in EGIII means a residue which exists in an equivalent position to that in EGIII, as indicated by primary sequence homology, tertiary structural homology (as shown by, e.g., crystal structure or computer modeling) or functional equivalence. A variant EGIII-like cellulase has an amino acid sequence that is derived from the amino acid sequence of a precursor EGIII-like cellulase. The precursor cellulases include naturally occurring cellulases and recombinant cellulases (as defined herein). The amino acid sequence of the EGIII-like cellulase variant is derived from the precursor EGIII-like cellulase amino acid sequence by the substitution, deletion or insertion of one or more amino acids of the precursor amino acid sequence. Such modification is of the precursor DNA sequence that encodes the amino acid sequence of the precursor cellulase rather than manipulation of the precursor cellulase enzyme per se. Suitable methods for such manipulation of the precursor DNA sequence include methods disclosed herein and in commonly owned U.S. Pat. Nos. 4,760,025 and 5,185,258. Specific residues corresponding to the positions that are responsible for instability in the presence of surfactant are identified herein for substitution or deletion. The amino acid position number (e.g., +35) refers to the number assigned to the mature *Trichoderma reesei* EGIII sequence presented in FIG. 1. The invention is directed to the mutation of EGIII-like cellulases that contain amino acid residues at positions that are equivalent to the particular identified residue in *Trichoderma reesei* EGIII. A residue (amino acid) of a precursor cellulase is equivalent to a residue of *Trichoderma reesei* EGIII if it is either homologous (i.e., corresponding in position in either primary or tertiary structure) or is functionally analogous to a specific residue or portion of that residue in *Trichoderma reesei* EGIII (i.e., having the same or similar functional capacity to combine, react, or interact chemically or structurally). As used herein, numbering is intended to correspond to that of the mature EGIII amino acid sequence as illustrated in FIG. 2.

To determine corresponding residues of EGIII-like cellulases from other organisms than *T. reesei*, a sequence alignment is generated as above with the EGIII-like cellulases. A residue at a known position in *T. reesei* is identified and located on the alignment. Corresponding residues of other EGIII-like cellulases can be determined. For example, a sequence alignment is shown in FIG. 3. The alanine at position 35 of mature EGIII corresponds to position 81 of the sequence alignment. A corresponding residue from *H. grisea* is aspartic acid.

Homologous proteins can also be determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acdd. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

An example of an algorithm that is suitable for determining sequence similarity is the BLAST algorithm, which is described in Altschul, et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

"Equivalent residues" may also be defined by determining homology at the level of tertiary structure for a precursor protease whose tertiary structure has been determined by x-ray crystallography. Equivalent residues are defined as those for which the atomic coordinates of two or more of the main chain atoms of a particular amino acid residue of a cellulase and *T. reesei* EGIII (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the cellulase in question to the *T. reesei* EGIII. The best model is the crystallographic model giving the lowest R factor for experimental diffraction data at the highest resolution available.

$$R\ factor = \frac{\sum_h |Fo(h)| - |Fc(h)|}{\sum_h |Fo(h)|}$$

Equivalent residues which are functionally analogous to a specific residue of *T. reesei* EGIII are defined as those amino acids of a cellulase which may adopt a conformation such that they either alter, modify or contribute to protein structure, substrate binding or catalysis in a manner defined and attributed to a specific residue of the *T. reesei* EGIII. Further, they are those residues of the cellulase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *T. reesei* EGIII.

The crystal structure of *T. reesei* EGIII is presented at The Protein Society, Fourteenth Symposium. San Diego, Calif. Aug. 5–9, 2000, the disclosure of which is incorporated by reference in its entirety. The coordinates of CelB of *Streptomyces lividans*, a homologous member of the Family 12 glycosyl hydrolases is provided in Sulzenbacher, et al., *Biochemistry* 36:6032 (1997) and in Sulzenbacher, et al., *Biochemistry* 38:4826 (1999).

"Variant" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of an enzyme variant is preferably achieved by modifying a DNA sequence which encodes for the native protein, transformation of that DNA sequence into a suitable host, and expression of the modified DNA sequence to form the derivative enzyme. The variant EGIII-like enzyme of the invention includes peptides comprising altered amino acid sequences in comparison with a precursor enzyme amino acid sequence wherein the variant EGIII-like enzyme retains the characteristic cellulolytic nature of the precursor enzyme but which may have altered properties in some specific aspect. For example, a variant EGIII-like enzyme may have an increased pH optimum or increased temperature or oxidative stability but will retain its characteristic cellulolytic activity. It is contemplated that the variants according to the present invention may be derived from a DNA fragment encoding a cellulase variant EGIII-like enzyme wherein the functional activity of the expressed cellulase derivative is retained. For example, a DNA fragment encoding a cellulase may further include a DNA sequence or portion thereof encoding a hinge or linker attached to the cellulase DNA sequence at either the 5' or 3' end wherein the functional activity of the encoded cellulase domain is retained.

"Expression vector" means a DNA construct comprising a DNA sequence that is operably linked to a suitable control sequence capable of effecting the expression of the DNA in a suitable host. Such control sequences may include a promoter to effect transcription, an optional operator sequence to control transcription, a sequence encoding suitable ribosome-binding sites on the mRNA, and sequences that control termination of transcription and translation. Different cell types are preferably used with different expression vectors. A preferred promoter for vectors used in *Bacillus subtilis* is the AprE promoter; a preferred promoter used in *E. coli* is the Lac promoter, a preferred promoter used in *Saccharomyces cerevisiae* is PGKl, a preferred promoter used in *Aspergillus niger* is glaA, and a preferred promoter for *Trichoderma reesei* is cbhI. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors that serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2 μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook. Often, such expression vectors including the DNA sequences of the invention are transformed into a unicellular host by direct insertion into the genome of a particular species through an integration event (see e.g., Bennett & Lasure, *More Gene Manipulations in Fungi*, Academic Press, San Diego, pp. 70–76 (1991) and articles cited therein describing targeted genomic insertion in fungal hosts, incorporated herein by reference).

"Host strain" or "host cell" means a suitable host for an expression vector comprising DNA according to the present invention. Host cells useful in the present invention are generally prokaryotic or eukaryotic hosts, including any transformable microorganism in which expression can be achieved. Preferred host strains include, but are not limited to, *Bacillus subtilis, Escherichia coli, Trichoderma reesei, Saccharomyces cerevisiae* or *Aspergillus niger*. A most preferred host is *A. niger*. Host cells are transformed or transfected with vectors constructed using recombinant DNA techniques. Such transformed host cells are capable of both replicating vectors encoding the variant EGIII-like enzymes or expressing the desired peptide product.

"Signal sequence" means a sequence of amino acids bound to the N-terminal portion of a protein that facilitates the secretion of the mature form of the protein outside of the cell. This definition of a signal sequence is a functional one. The mature form of the extracellular protein lacks the signal sequence that is cleaved off during the secretion process.

"DNA vector" means a nucleotide sequence which comprises one or more DNA fragments or DNA variant fragments encoding an EGIII-like cellulase or variants described above which can be used, upon transformation into an appropriate host cell, to cause expression of the variant EGIII-like cellulase.

"Functionally attached to" means that a regulatory region, such as a promoter, terminator, secretion signal or enhancer region is attached to a structural gene and controls the expression of that gene.

The present invention relates to the expression, purification and/or isolation and use of variant EGIII-like cellulases. These enzymes are preferably prepared by recombinant methods utilizing the gene identified and isolated according to the methods described above. However, enzymes for use in the present invention may be obtained by other art-recognized means such as purification from natural isolates.

The microorganism to be transformed for the purpose of expressing an EGIII-like cellulase according to the present invention may advantageously comprise a strain derived from *Trichoderma reesei* sp. Thus, a preferred mode for preparing EGIII-like cellulases according to the present invention comprises transforming a Trichoderma sp. host cell with a DNA construct comprising at least a fragment of DNA encoding a portion or all of the EGIII-like cellulase detected as described above. The DNA construct will generally be functionally attached to a promoter. The transformed host cell is then grown under conditions so as to express the desired protein. Subsequently, the desired protein product is purified to substantial homogeneity.

In an alternative embodiment, *Aspergillus niger* can be used as an expression vehicle. For a description of transformation techniques with *A. niger*, see WO 98/31821, the disclosure of which is incorporated by reference in its entirety.

In one embodiment, the strain comprises *T. reesei* (*reesei*) which is a useful strain for obtaining overexpressed protein. For example, RL-P37, described by Sheir-Neiss, et al., *Appl. Microbiol. Biotechnol.* 20:46–53 is known to secrete elevated amounts of cellulase enzymes. Functional equivalents of RL-P37 include *Trichoderma reesei* (*reesei*) strain RUT-C30 (ATCC No. 56765) and strain QM9414 (ATCC No. 26921). It is contemplated that these strains would also be useful in overexpressing EGIII-like cellulases.

Where it is desired to obtain the EGIII-like cellulase in the absence of potentially detrimental native cellulolytic activity, it is useful to obtain a Trichoderma host cell strain which has had one or more cellulase genes deleted prior to introduction of a DNA construct or plasmid containing the DNA fragment encoding the EGIII-like cellulase. Such strains may be prepared by the method disclosed in U.S. Pat. No. 5,246,853 and WO 92/06209, which are hereby incorporated by reference. By expressing an EGIII-like cellulase in a host microorganism that is missing one or more cellulase genes, the identification and subsequent purification procedures are simplified. Any gene from Trichoderma sp. which has been cloned can be deleted, for example, the cbh1, cbh2, egl1, and egl3 genes as well as those encoding EGIII and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with Trichoderma sp., the selectable marker is chosen so that the presence of the selectable marker in the transformants will not significantly affect the properties of the fungus. Such a selectable marker may be a gene that encodes an assayable product. For example, a functional copy of a Trichoderma sp. gene may be used which if lacking in the host strain results in the host strain displaying an auxotrophic phenotype.

In a preferred embodiment, a pyr4⁻ derivative strain of Trichoderma sp. is transformed with a functional pyr4 gene, which thus provides a selectable marker for transformation. A pyr4⁻ derivative strain may be obtained by selection of Trichoderma sp. strains that are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to selectpyr4⁻ derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges & Barreau, *Curr. Genet.* 9:359–365 (1991)). Selection of derivative strains is easily performed using the FOA resistance technique referred to above, and thus, the pyr4 gene is preferably employed as a selectable marker.

To transform pyr4⁻ Trichoderma sp. so as to be lacking in the ability to express one or more cellulase genes, a single DNA fragment comprising a disrupted or deleted cellulase gene is then isolated from the deletion plasmid and used to transform an appropriate pyr⁻ Trichoderma host. Transformants are then identified and selected based on their ability to express the pyr4 gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the pyr4 selectable markers.

Although the specific plasmid vectors described above relate to preparation of pyr⁻ transformants, the present invention is not limited to these vectors. Various genes can be deleted and replaced in the Trichoderma sp. strain using the above techniques. In addition, any available selectable markers can be used, as discussed above. In fact, any Trichoderma sp. gene that has been cloned, and thus identified, can be deleted from the genome using the above-described strategy.

As stated above, the host strains used are derivatives of Trichoderma sp. that lack or have a nonfunctional gene or genes corresponding to the selectable marker chosen. For example, if the selectable marker of pyr4 is chosen, then a specific pyr4⁻ derivative strain is used as a recipient in the transformation procedure. Similarly, selectable markers comprising Trichoderma sp. genes equivalent to the *Aspergillus nidulans* genes amdS, argB, trpC, niaD may be used. The corresponding recipient strain must therefore be a derivative strain such as argB⁻, trpC⁻, niaD⁻, respectively.

DNA encoding the EGIII-like cellulase is then prepared for insertion into an appropriate microorganism. According to the present invention, DNA encoding an EGIII-like cellulase comprises the DNA necessary to encode for a protein that has functional cellulolytic activity. The DNA fragment or DNA variant fragment encoding the EGIII-like cellulase or derivative may be functionally attached to a fungal promoter sequence, for example, the promoter of the cbh1 or egl1 gene.

It is also contemplated that more than one copy of DNA encoding a EGIII-like cellulase may be recombined into the strain to facilitate overexpression. The DNA encoding the EGIII-like cellulase may be prepared by the construction of an expression vector carrying the DNA encoding the cellulase. The expression vector carrying the inserted DNA fragment encoding the EGIII-like cellulase may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences. For example, pTEX is such a general-purpose expression vector. Genes or part thereof can be inserted downstream of the strong cbh1 promoter.

In the vector, the DNA sequence encoding the EGIII-like cellulase of the present invention should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. The signal peptide provides for extracellular production of the EGIII-like cellulase or derivatives thereof. The DNA encoding the signal sequence is preferably that which is naturally associated with the gene to be expressed, however the signal sequence from any suitable source, for example an exo-cellobiohydrolase or endoglucanase from Trichoderma, is contemplated in the present invention.

The procedures used to ligate the DNA sequences coding for the EGIII-like cellulase of the present invention with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in Trichoderma sp. is very low. Accordingly, uptake of the desired DNA sequence, gene or gene fragment is at best minimal. There are a number of methods to increase the permeability of the Trichoderma sp. cell wall in the derivative strain (i.e., lacking a functional gene corresponding to the used selectable marker) prior to the transformation process.

The preferred method in the present invention to prepare Trichoderma sp. for transformation involves the preparation of protoplasts from fungal mycelium. The mycelium can be obtained from germinated vegetative spores. The mycelium is treated with an enzyme that digests the cell wall resulting in protoplasts. The protoplasts are then protected by the presence of an osmotic stabilizer in the suspending medium.

These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host Trichoderma sp. strain is dependent upon the calcium ion concentration. Generally, between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the Trichoderma sp. strain and the plasmid DNA is transferred to the nucleus. This fusion frequently leaves multiple copies of the plasmid DNA tenderly integrated into the host chromosome.

Usually a suspension containing the Trichoderma sp. protoplasts or cells that have been subjected to a permeability treatment at a density of $10^8$ to $10^9$/ml, preferably $2 \times 10^8$/ml are used in transformation. A volume of 100 microliters of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated at room temperature before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if $Pyr^+$ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may be made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the EGIII-like cellulases or derivatives thereof are recovered in active form from the host cell after growth in liquid media either as a result of the appropriate post translational processing of the novel EGIII-like cellulase or derivatives thereof.

The expressed EGIII-like cellulase may be recovered from the medium by conventional techniques including separations of the cells from the medium by centrifugation, filtration, and precipitation of the proteins in the supernatant or filtrate with a salt, for example, ammonium sulphate. Additionally, chromatography procedures such as ion exchange chromatography or affinity chromatography may be used. Antibodies (polyclonal or monoclonal) may be raised against the natural purified EGIII-like cellulase, or synthetic peptides may be prepared from portions of the EGIII-like cellulase molecule and used to raise polyclonal antibodies.

Although it is preferred that substitutions of residues from thermally more stable EG III-like cellulases into EG III cellulase result in more stable EG III, that is not the only possible useful outcome. To one of skill, it will be apparent that substitutions that result in less stable EG III cellulases are also useful in, e.g., compositions used to treat delicate textiles and in other applications where the prolonged existence of active EG III is not desired. In addition, one of skill will readily appreciate that converse substitutions are useful. For example, residues from less thermally stable EG III can be substituted into more stable EG III like cellulases to make less (or more) stable EG III homologs. Again, less stable homologs can be used when the prolonged presence of active cellulase is not required.

Treatment of textiles according to the present invention contemplates textile processing or cleaning with a composition comprising a cellulase. Such treating includes, but is not limited to, stonewashing, modifying the texture, feel and/or appearance of cellulose containing fabrics or other techniques used during manufacturing or cleaning/reconditioning of cellulose containing fabrics. Additionally, treating within the context of this invention contemplates the removal of "immature" or "dead" cotton, from cellulosic fabric or fibers. Immature cotton is significantly more amorphous than mature cotton and results in a lesser quality fabric when present due to, for example, uneven dyeing. The composition contemplated in the present invention further includes a cellulase component for use in washing of a soiled manufactured cellulose containing fabric. For example, the cellulase may be used in a detergent composition for washing laundry. Detergent compositions useful in accordance with the present invention include special formulations such as pre-wash, pre-soak and home-use color restoration compositions. Such treating compositions, as described herein, may be in the form of a concentrate which requires dilution or in the form of a dilute solution or form which can be applied directly to the cellulose containing fabric. General treatment techniques for cellulase treatment of textiles are described in, for example, EP Publication No. 220 016 and GB Application Nos. 1,368,599 and 2,095,275.

Treatment of a cellulosic material according to the present invention further contemplates the treatment of animal feed, pulp and/or paper, food and grain for purposes known in the art. For example, cellulase is known to increase the value of animal feed, improve the drainability of wood pulp, enhance food products and reduce fiber in grain during the grain wet milling process or dry milling process.

Treating, according to the instant invention, comprises preparing an aqueous solution that contains an effective amount of cellulase together with other optional ingredients including, for example, a buffer, a surfactant, and/or a scouring agent. An effective amount of cellulase enzyme composition is a concentration of cellulase enzyme sufficient for its intended purpose. Thus, for example, an "effective amount" of cellulase in a stonewashing composition according to the present invention is that amount which will provide the desired effect, e.g., to produce a worn and faded look in the seams and on fabric panels. Similarly, an "effective amount" of cellulase in a composition intended for improving the feel and/or appearance of a cellulose containing fabric is that amount which will produce measurable improvements in the feel, e.g., improving the smoothness of the fabric, or appearance, e.g., removing pills and fibrils which tend to reduce the sharpness in appearance of a fabric. The amount of cellulase employed is also dependent on the equipment employed, the process parameters employed (the temperature of the cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric to be treated is added can be readily determined by the skilled artisan based on the above factors as well as the desired result. In stonewashing processes, it has generally been preferred that the cellulase be present in the aqueous treating solution in a concentration of from about 0.5 to 5,000 ppm and most preferably about 10 to 200 ppm total protein. In compositions for the improvement of feel and/or appearance of a cellulose containing fabric, it has generally been preferred that the cellulase be present in the aqueous treating solution in a concentration of from about 0.1 to 2000 ppm and most preferably about 0.5 to 200 ppm total protein.

In a preferred treating embodiment, a buffer is employed in the treating composition such that the concentration of buffer is sufficient to maintain the pH of the solution within the range wherein the employed cellulase exhibits activity which, in turn, depends on the nature of the cellulase employed. The exact concentration of buffer employed will depend on several factors that the skilled artisan can readily take into account. For example, in a preferred embodiment, the buffer, as well as the buffer concentration, is selected so as to maintain the pH of the final cellulase solution within the pH range required for optimal cellulase activity. The determination of the optimal pH range of the cellulases of the invention can be ascertained according to well-known techniques. Suitable buffers at pH within the activity range of the cellulase are well known to those skilled in the art in the field.

In addition to cellulase and a buffer, the treating composition may optionally contain a surfactant. Suitable surfactants include any surfactant compatible with the cellulase and the fabric including, for example, anionic, non-ionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

A concentrated cellulase composition can be prepared for use in the methods described herein. Such concentrates contain concentrated amounts of the cellulase composition described above, buffer and surfactant, preferably in an aqueous solution. When so formulated, the cellulase concentrate can readily be diluted with water so as to quickly and accurately prepare cellulase preparations having the requisite concentration of each constituent. When aqueous concentrates are formulated, these concentrates can be diluted so as to arrive at the requisite concentration of the components in the cellulase solution as indicated above. As is readily apparent, such cellulase concentrates will permit facile formulation of the cellulase solutions as well as permit feasible transportation of the composition to the location where it will be used. The treating concentrate can be in any art recognized form, for example, liquid, emulsion, gel, or paste. Such forms are well known to those skilled in the art.

When a solid cellulase concentrate is employed, the cellulase composition may be a granule, a powder, an agglomerate or a solid disk. The granules can be formulated so as to contain materials to reduce the rate of dissolution of the granules into the wash medium. Such materials and granules are disclosed in U.S. Pat. No. 5,254,283, which is incorporated herein by reference in its entirety.

Other materials can also be used with or placed in the cellulase composition of the present invention as desired, including stones, pumice, fillers, solvents, enzyme activators, and anti-redeposition agents depending on the eventual use of the composition.

By way of example, stonewashing methods will be described in detail, however, the parameters described are readily modified by the skilled artisan for other applications, e.g., improving the feel and/or appearance of a fabric. The cellulose containing fabric is contacted with the cellulase containing stonewashing composition containing an effective amount of the cellulase by intermingling the treating composition with the stonewashing composition, and thus bringing the cellulase enzyme into proximity with the fabric. Subsequently, the aqueous solution containing the cellulase and the fabric is agitated. If the treating composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor.

The cellulose containing fabric is incubated with the stonewashing solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature that allow the cellulase enzyme to react efficiently with cellulose containing fabric, in this case to produce the stonewashed effect. However, such conditions are readily ascertainable by one of skill in the art. The reaction conditions effective for the stonewashing compositions of the present invention are substantially similar to well known methods used with corresponding prior art cellulase compositions. Accordingly, it is within the skill of those in the art to maximize conditions for using the stonewashing compositions according to the present invention.

The liquor ratios during stonewashing, i.e., the ratio of weight of stonewashing composition solution (the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from about 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature, which temperature is dependent on the nature of the cellulase used. Thus, if the reaction temperature is permitted to go too high, the cellulolytic activity is lost as a result of the denaturing of the cellulase. While standard temperatures for cellulase usage in the art are generally in the range of 35° C. to 65° C., which conditions would also be expected to be suitable for the cellulase of the invention, the optimal temperature conditions should be ascertained according to well known techniques with respect to the specific cellulase used.

Reaction times are dependent on the specific conditions under which the stonewashing occurs. For example, pH, temperature and concentration of cellulase will all affect the optimal reaction time. Generally, reaction times are from about 5 minutes to about 5 hours, and preferably from about 10 minutes to about 3 hours and, more preferably, from about 20 minutes to about 1 hour.

According to yet another preferred embodiment of the present invention, the cellulase of the invention may be employed in a detergent composition. The detergent compositions according to the present invention are useful as pre-wash compositions, pre-soak compositions, or for cleaning during the regular wash or rinse cycle. Preferably, the detergent composition of the present invention comprises an effective amount of cellulase, a surfactant, and optionally includes other ingredients described below.

An effective amount of cellulase employed in the detergent compositions of this invention is an amount sufficient to impart the desirable effects known to be produced by cellulase on cellulose containing fabrics, for example, depilling, softening, anti-pilling, surface fiber removal, anti-graying and cleaning. Preferably, the cellulase in the detergent composition is employed in a concentration of from about 10 ppm to about 20,000 ppm of detergent.

The concentration of cellulose enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The amount of cellulase enzyme employed in the detergent composition will depend on the extent to which the detergent will be diluted upon addition to water so as to form a wash solution.

The detergent compositions of the present invention may be in any art recognized form, for example, as a liquid, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase-protecting agent. The granule can be formulated so as to contain materials to reduce the rate of dissolution of the granule into the wash medium. Such materials and granules are disclosed in U.S. Pat. No. 5,254,283, which is incorporated herein by reference in its entirety.

The detergent compositions of this invention employ a surface-active agent, e.g., a surfactant, including anionic, non-ionic and ampholytic surfactants well known for their use in detergent compositions. The detergent composition of the present invention can be used in a broad pH range from acidic to alkaline pH. In a preferred embodiment, the detergent composition of the present invention can be used in mildly acidic, neutral or alkaline detergent wash media having a pH of from above 5 to no more than about 12.

Aside from the above ingredients, perfumes, buffers, preservatives, dyes, and the like can be used, if desired, with the detergent compositions of this invention. Such components are conventionally employed in amounts heretofore used in the art.

The use of the cellulase according to the invention may also be particularly effective in feed additives and in the processing of pulp and paper. These additional industrial applications are described in, for example, PCT Publication No. 95/16360 and Finnish Granted Patent No. 87372, respectively.

In order to further illustrate the present invention and advantages thereof, the following specific examples are given with the understanding that they are being offered to illustrate the present invention and should not be construed in any way as limiting its scope.

EXAMPLES

Example 1

Preparation of Genomic DNA Encoding EGIII-Like Cellulases

Genomic DNA was prepared for several different microorganisms for the purpose of undertaking a PCR reaction to determine whether EGIII-like cellulases are encoded by the DNA of a particular organism.

Genomic DNA was obtained from Acremonium brachypenium deposit no. CBS 866.73; *Chaetomium brasillience* deposit no. CBS 140.50; *Chaetomium vitellium* deposit no. CBS 250.85; *Emericella desertoru* deposit no. CBS 653.73; *Fusarium equiseti* deposit no. CBS 185.34; *Gliocladium roseum* deposit no. CBS 443.65; *Humicola grisea* var. thermoidia deposit no. CBS 225.63; *Myceliopthora thermophila* deposit no. ATCC 48102–48104; *Penicillium notatum* deposit no. ATCC 9178, 9179; and *Phanerochaete chrysosporium* deposit no. ATCC 28326 and isolated according to standard methods.

PCR was performed on a standard PCR machine such as the PCT-150 MicroCycler from MJ Research Inc. under the following conditions:

1) 1 minute at 98° C. for 1 cycle;
2) 1 minute at 94° C.,
   90 seconds at 40° C.,
   1 minute at 72° C.
3) repeat step 2 for 30 cycles,
4) 7 minutes at 72° C. for 1 cycle, and
5) lower temperature to 15° C. for storage and further analysis.

The following DNA primers were constructed for use in amplification of EGIII-like genes from the libraries constructed from the various microorganisms. All symbols used herein for protein and DNA sequences correspond to IUPAC IUB Biochemical Nomenclature Commission codes.

```
BOX1: primers coding for (N/Q)NLWG (SEQ ID NO:30)

forward primer      FRG001: AAY AAY YTN TGG GG
                    (SEQ ID NO:31)
forward primer      FRG002: CAR AAY YTN TGG GG
                    (SEQ ID NO:32)
BOX1': primers coding for NNN(F/L/Y/I/L/N/K)WG
(SEQ ID NO:33)

forward primer      FRG010: AAY AAY AAY HWI TGG GG
                    (SEQ ID NO:34)
BOX2: primers coding for ELMIW (SEQ ID NO:35)

forward primer      FRG003: GAR YTN ATG ATH TGG
                    (SEQ ID NO:36)
reversed primer     FRG004: CCA DAT CAT NAR YTC
                    (SEQ ID NO:37)
BOX2': primers coding for YELMIW (SEQ ID NO:38)

forward primer      FRG011: TAY GAR YTI ATG ATH TGG
                    (SEQ ID NO:39)
reversed primer     FRG012: CCA DAT CAT IAR YTC RTA
                    (SEQ ID NO:40)
BOX3: primers coding for GTE(P/C)FT
(SEQ ID NO:41)

reversed primer     FRG005: GTR AAN GGY TCR GTR CC
                    (SEQ ID NO:42)
reversed primer     FRG006: GTR AAN GGY TCR GTY CC
                    (SEQ ID NO:43)

reversed primer     FRG007: GTR AAN GGY TCY GTR CC
                    (SEQ ID NO:44)
reversed primer     FRG008: GTR AAN GGY TCY GTY CC
                    (SEQ ID NO:45)
reversed primer     FRG009: GTR AAR CAY TCN GTN CC
                    (SEQ ID NO:46)
```

PCR conditions were as follows: 10 µL of 10×reaction buffer (10×reaction buffer comprising 100 mM Tris HCl, pH 8–8.5; 250 mM KCl; 50 mM $(NH_4)_2SO_4$; 20 mM $MgSO_4$); 0.2 mM each of DATP, dTTP, dGTP, dCTP (final concentration), 1 µL of 100 ng/µL genomic DNA, 1 µL of PWO polymerase (Boehringer Mannheim, Cat #1644–947) at 1 unit per µL, 500 mM primers (final concentration) and water to 100 µL. The solution was overlaid with mineral oil.

The PCR strategy was as follows: forward primers for BOX1 (SEQ ID NO:31 and 32 respectively) and BOX1' (SEQ ID NO:34) were combined with reversed primers from BOX3 (SEQ ID NO:42–46) in a mixture with the desired genomic DNA sample and run on a gel to obtain fragments in the 400–1000 base pair range. The fragments so obtained were pooled and the pool split into two approximately equal portions. The first pool was combined with the forward primers from BOX1 (SEQ ID NO:31 and 32 respectively) and BOX1' (SEQ ID NO:34) along with the reversed primer from BOX2 (SEQ ID NO:37). The second pool was combined with the forward primer from BOX2 (SEQ ID NO:36) along with the reversed primers from BOX3 (SEQ ID NO:42–46). Fragments having the approximate size relative to an EGIII-like cellulase considering the location of the primers within the gene, in this case corresponding to those between 250–500 base pairs, were isolated and sequenced.

From the sequenced fragments, it was possible to use the RAGE technique (rapid amplification of genomic ends) to rapidly obtain the sequence of the full-length gene. Full-length genes have been obtained and are provided with several additional EGIII-like cellulase sequences in FIG. 3. As shown in FIG. 3, full length genes isolated from *Hypocrea schweinitzii* (SEQ ID NO:4), *Aspergillus aculeatus* (SEQ ID NO:5), *Aspergillus kawachii* (1) (SEQ ID NO:6), *Aspergillus kawachii* (2) (SEQ ID NO:7), *Aspergillus oryzae* (SEQ ID NO:8), *Humicola grisea* (SEQ ID NO:9), *Humicola insolens* (SEQ ID NO:10), *Chaetomium brasilliense* (SEQ ID NO:11), *Fusarium equiseti* (SEQ ID NO:12), *Fusarium javanicum* (1) (SEQ ID NO:13), *Fusarium javanicum* (2) (SEQ ID NO:14), *Gliocladium roseum* (1) (SEQ ID NO:15), *Gliocladium roseum* (2) (SEQ ID NO:16), *Gliocladium roseum* (3) (SEQ ID NO:17), *Gliogladium roseum* (4) (SEQ ID NO:18), *Memnoniella echinata* (SEQ ID NO:19), Actinomycete 11AG8 (SEQ ID NO:21), *Streptomyces lividans* CelB (SEQ ID NO:22), *Rhodothermus marinus* (SEQ ID NO:23), *Emericella desertoru* (SEQ ID NO:20), and *Erwinia carotovara* (SEQ ID NO:24) all comprised significant homology to EGIII from *Trichoderma reesei*.

Example 2

Temperature Stability Testing of EGIII and EGIII Like Cellulases

EGIII and EGIII homologs derived from *Humicola grisea*, *Humicola insolens*, *Emercella desertoru*, *Fusarium javanicum* and *Memnonella echinata* were tested to determine their stability under temperature stress.

Stability was assayed by following the rate of loss of activity upon incubation at a fixed, high temperature: Solutions of EGIII and EGIII-like cellulases at between 0.1 mg/ml and 0.5 mg/ml in 50 mM citrate/phosphate buffer at pH8.0 were incubated in a water bath at 48° C. At measured times 100 µl aliquots were removed and cooled (or frozen) rapidly. The remaining activity in these aliquots was assayed as detailed below. An irreversible thermal inactivation curve was generated by plotting remaining activity vs time, and the data fitted to a single exponential decay. The half-time of this exponential decay was determined as a measure of thermal stability.

The activity assay was performed as follows: In a well of a 96-well micro-titer plate, 10 µL of enzyme sample was added to 120 µL of substrate (4.2 mg/ml o-nitrophenyl cellobioside) in 50 mM potassium phosphate, pH 6.7. The plate was then incubated for 10 min at 40° C., and the reactions quenched with 70 µL of 0.2M glycine. The absorption at 410 nm (due to the o-nitrophenol released upon enzymatic cleavage of the substrate) was measured in a micro-titer plate reader. This end-point 410 nm reading was proportional to the cellulase activity in the enzyme sample.

The results of the stability testing were as shown in Table 1:

TABLE 1

| EG III LIKE ENZYME | HALF LIFE (MINUTES) |
| --- | --- |
| *H. grisea* | stable* |
| *H. insolens* | stable* |
| *E. desertoru* | 200 |
| *F. javanicum* | 93 |
| *M. echinata* | 192 |
| *T. reesei* (EGIII) | 23 |

*"stable" indicates less than 20% loss in activity in 200 mins.

As can be seen by the above results, the EGIII-like cellulases had significantly improved stability despite being relatively homologous to EGIII from *T. reesei*. Accordingly, it is apparent the residues that are different in the more stable homologs are critical for the improved stability of the EGIII-like cellulases and, as such, further improvement of the EGIII-like cellulases and EGIII itself by modifying these residues will result in additional improvements in the stability of EGIII and the EGIII-like enzymes.

Example 3

Stability of *T. reesei* and *H. grisea* variant EGIII-like Cellulases

Site-directed mutagenesis was performed to incorporate amino acid substitutions in *T. reesei* EGIII. The amino acids substituted into the EGIII were those at homologous locations in the *H. grisea* homolog.

The following primers were used to produce cysteine substitutions in EGIII from *T. reesei* and in the EGIII-like cellulase from *H. grisea*. PCR was performed according to well-known techniques.

sion vector pGAPT-pyrG. This is a variant of PGPT-pyrG (Berka and Barnett, *Biotech.Adv.* 7:127 (1989)) in which non-essential DNA has been excised. Vectors carrying the variant genes were then transformed into *A.niger* var. awamori and the resultant strains grown in shake-flask cultures (WO 98/31821).

EG III and EGIII-like cellulase variants were then purified from cell-free supernatants of these cultures by column chromatography. Briefly, approximately 1 mL of Pharmacia Butyl Sepharose (Fast Flow) resin per 10 mg of EGIII was loaded into a disposable drip column with 0.5 M. ammonium sulfate. The column was then equilibrated with 0.05 M Bis Tris Propane and 0.05 M ammonium acetate at pH 8 with 0.5 M ammonium sulphate.

The EGIII-like cellulase containing supernatants were treated overnight with 0.18 mg/mL of endoglucanase H at 37° C. Ammonium sulfate was added to the treated supernatants to a final concentration of approximately 0.5 M. After centrifugation, the supernatant was loaded onto the column. The column was then washed with 3 volumes equilibration buffer and then eluted with 2×1 volumes of

| EGIII-like cellulase | Variant | Forward primer | Reverse Primer |
|---|---|---|---|
| T. reesei | V210C | GGA ACT CTG AAC TGC GCA TGG TGG ACC (SEQ ID NO:47) | GGT CCA GGA TGC GCA GTT CAG AGT TCC (SEQ ID NO:48) |
| | G170C | CCA ACT ACA GCT GTG ATG TCA AGA AC (SEQ ID NO:49) | GTT CTT GAC ATC ACA GCT GTA GTT GG (SEQ ID NO:50) |
| | P201C | CCA ATT TGG TAC CGA GTG CTT CAC GGG CAG TG (SEQ ID NO:51) | CAC TGC CCG TGA AGC ACT CGG TAC CAA ATT GG (SEQ ID NO:52) |
| H. grisea | C231V | CCA GGT TCA CGG TCA GGG ACT TCA GG (SEQ ID NO:53) | CCT GAA GTC CCT GAC CGT GAA CCT GG (SEQ ID NO:54) |
| | C190G | CGT GAC TTC AGC GGT GAC ATC AAG GAC (SEQ ID NO:55) | GTC CTT GAT GTC ACC GCT GAA GTC ACG (SEQ ID NO:56) |
| | C221S | GTC GGA ACA GAG TCC TTC ACA GGC GGT C (SEQ ID NO:57) | GAC CGC CTG TGA AGG ACT CTG TTC CGA C (SEQ ID NO:58) |
| | C221P | GTC GGA ACA GAG CCC TTC ACA GGC GGT C (SEQ ID NO:59) | GAC CGC CTG TGA AGG GCT CTG TTC CGA C (SEQ ID NO:60) |
| | C231S | CCA GGT TCA CGA GCA GGG ACT TCA GG (SEQ ID NO:61) | CCT GAA GTC CCT GCT CGT GAA CCT GG (SEQ ID NO:62) |
| | C190S | CGT GAC TTC AGC AGT GAC ATC AAG GAC (SEQ ID NO:63) | GTC CTT GAT GTC ACT GCT GAA GTC ACG (SEQ ID NO:64) |

Briefly, DNA that encodes *T. reesei* EG III or *H. grisea* EGIII-like cellulase was amplified from a cDNA clone (Ward, et al., *Proc. of the Tricel Symposium on "Trichoderma reesei cellulases and other hydrolases."* Espoo, Finland 1993 Ed. Suominen, P. and Reinikanen, T. Foundation for Biotechnical and Industrial Research. 8, pp153–158.; and U.S. Pat. No. 5,475,101) using PCR primers that introduced a Bgl II restriction endonuclease site at the 5' end of the egl3 gene (immediately upstream of the first ATG codon) and an Xba I site at the 3' end (immediately downstream of the "stop" codon). The amplified fragment was then digested with Bgl II and Xba I, and ligated into pUC19 digested with Bgl II and Xba I.

Variants were made in this plasmid using the QuikChange™ mutagenesis methods (Stratagene). The variant genes were then subcloned into the Aspergillus expres- 0.05 M Bis Tris Propane and 0.05 M ammonium acetate, pH 8. Each volume of flow through was collected as a separate fraction with the EGIII-like cellulase appearing in the second fraction.

Equilibrium CD experiments were performed on an Aviv 62DS or 62ADS spectrophotometer, equipped with a 5 position thermoelectric cell holder supplied by Aviv. Buffer conditions were 50 mM bis-tris propane and 50 mM ammonium acetate adjusted to pH 8.0 with acetic acid. The final protein concentration for each experiment was in the range of 5–30 $\mu$M. Data was collected in a 0.1 cm path length cell.

Spectra were collected from 265~210 nm. Thermal denaturations were performed at 217 nm from 30 to 90° C. with data collected every two degrees. The equilibration time at each temperature was 0.1 minutes and data was collected for 4 seconds per sample.

The remainder of the pH 8.0 sample was divided into 5×400 uL aliquots. Two samples were adjusted to pH 5 and 7 with acetic acid and two others were adjusted to pH 9 and 10 with sodium hydroxide. Thermal denaturations of all five samples were performed simultaneously as described above. The melting points were determined according to the methods of Luo, et al., *Biochemistry* 34:10669 and Gloss, et al, *Biochemistry* 36:5612.

TABLE 3

Thermal Stability of EGIII-like cellulases

| | EG III Residue Substitution | Δ Tm | Tm °C. | Fit error | Ave. Tm (std. dev.) | Ave. Fit error (std. dev.) |
|---|---|---|---|---|---|---|
| T. reesei | WT | 0.00 | 54.60 | 0.18 | 54.43 (0.21) | 0.20 (0.02) |
| | P201C | 3.9 | 58.3 | 0.15 | | |
| | | 17.4 | 71.8 | 0.23 | | |
| | G170C | 2.07 | 56.50 | 0.22 | | |
| | V210C | | 70.60 | 0.47 | 70.80 (0.72) | 0.31 (0.20) |
| | | 16.37 | 71.60 | 0.38 | | |
| | | | 70.20 | 0.09 | | |
| | G170C/ P201C | 0.67 | 55.1 | 0.11 | | |
| | P201C/ V210C | 0.69 | 55.12 | 0.09 | | |
| H. grisea | WT | 0.00 | 68.69 | 0.33 | | |
| | C231V | 0.78 | 69.47 | 0.33 | | |
| | C190G | 1.28 | 69.97 | 0.19 | | |
| | C221S | −5.43 | 63.26 | 0.12 | | |
| | C221P | −9.14 | 59.55 | 0.19 | | |
| | C231S | −5.55 | 63.14 | 0.18 | | |
| | C190S | 0.22 | 68.91 | 0.76 | | |

As can be seen, recruiting the cysteines from *H. grisea* EGIII-like cellulase into *T. reesei* EGIII increased the thermal stability of the variant EGIII-like cellulase compared to wild type. As expected, recruiting residues from EGIII or other EGIII like cellulases into H grisea EGIII-like cellulase decreased or had no effect on the thermal stability of the H grisea variant EGIII-like cellulase.

Example 4

Specific Activity of EGIII-like Cellulases

To assay for specific activity, a NPC hydrolysis assay was used. In a microtiter plate, 100 μl 50 mM sodium acetate, pH 5.5 and 20 μl 25 mg/mL o-NPC (o-Nitrophenyl o-D-Cellobioside (Sigma N 4764)) in assay buffer was added. The plate was incubated for 10 minutes at 40° C.

Once equilibrated, 10 μL EGIII-like cellulase was added and the plate incubated at 40° C. for another 10 minutes. To quench the hydrolysis and stop the reaction, 70 μL of 0.2 M glycine, pH 10.0 was added. The plate was then read in a microtiter plate reader at 410 nm. As a guide, 10 μL of a 0.1 mg/ml solution of *T. reesei* EGIII provided an OD of around 0.3.

The concentration of EGIII-like cellulase was determined by absorbance at 280 nm where the extinction coefficient was 78711 $M^{-1}$ $cm^{-1}$ or 3.352 $g/L^{-1}$ experimentally determined by the method of Edelhoch as described in Pace, et al., *Pro. Sci.* 4:2411 (1995).

TABLE 4

Specific Activity of EGIII-like Cellulases

| | EGIII-like Cellulase | Tm (° C.) | Specific Activity (relative to WT) | Standard Deviation |
|---|---|---|---|---|
| T. reesei | Wild Type | 54.43 | 1.00 | |
| | P201C | 58.3/71.8 | 0.21 | |
| | G170C | 56.5 | 0.68 | |
| | V210C | 70.8 | 0.13 | |
| H. grisea | WT | 68.7 | 1.00 | 0.032 |
| | C231V | 69.5 | 0.68 | 0.031 |
| | C190G | 70.0 | 0.65 | 0.134 |
| | C221S | 63.3 | 1.54 | 0.047 |
| | C221P | 59.6 | 0.91 | 0.040 |
| | C231S | 63.3 | 0.64 | 0.72 |
| | C190S | 68.5 | 0.02 | |

As can be seen from Table 4, the variants with mutations that stabilize the EGIII-like cellulases derived from EGIII lose activity. However, it is anticipated that other mutations will restore the activity and maintain the increased thermal stability of the EGIII-like cellulases.

Interestingly, the EGIII-like cellulases from *H. grisea* that lost the most thermal stability upon recruitment of EGIII residues maintained specific activity, and in instance, the mutation increased the specific activity of the EGIII-like cellulase.

We claim:

1. A variant EGIII or EGIII-like celulase consisting of a substitution at a position corresponding to one or more of residues P201, G170 and/or V210 in EGIII from *Trichoderma reesei* (SEQ ID NO:1).

2. The variant cellulase of claim 1, wherein said EGIII variant comprises a substitution at a position corresponding to one or more of residues P201C, G170C and/or V210C in EGIII.

3. The variant cellulose according to claim 1, wherein said cellulase is an endoglucanase.

4. A detergent composition comprising a surfactant and a cellulase, wherein said cellulase comprises a variant EGIII-like cellulase consisting of a substitution at a position corresponding to one or more of residues P201, G170 and/or V210 in EGIII from *Trichoderma reesei* (SEQ ID NO:1).

5. The detergent of claim 4, wherein said variant comprises a substitution at a position corresponding to one or more of residues residues P201C, G170C and/or V210C in EGIII.

6. The detergent according to claim 5, wherein said detergent is a laundry detergent.

7. The detergent according to claim 5, wherein said detergent is a dish detergent.

8. A method of treating a cellulose containing textile comprising contacting said textile with a variant EGIII or EGIII-like cellulose according to claim 1.

9. The method according to claim 8, wherein the treatment is stonewashing of indigo dyed denim.

10. A feed additive comprising a variant EGIII or EGIII-like cellulase according to claim 1.

11. A method of treating wood pulp comprising contacting said wood pulp with a variant EGIII or EGIII-like cellulose according to claim 1.

12. A method of converting biomass to glucose comprising contacting said biomass with a variant EGIII or EGIII-like cellulase according to claim 1.

\* \* \* \* \*

```
                        SEQUENCE LISTING

<160> NUMBER OF SEQ ID NOS: 64

<210> SEQ ID NO 1
<211> LENGTH: 218
<212> TYPE: PRT
<213> ORGANISM: Trichoderma reesei

<400> SEQUENCE: 1

Gln Thr Ser Cys Asp Gln Trp Ala Thr Phe Thr Gly Asn Gly Tyr Thr
  1               5                  10                  15

Val Ser Asn Asn Leu Trp Gly Ala Ser Ala Gly Ser Gly Phe Gly Cys
             20                  25                  30

Val Thr Ala Val Ser Leu Ser Gly Gly Ala Ser Trp His Ala Asp Trp
```

```
              35                  40                  45
Gln Trp Ser Gly Gly Gln Asn Asn Val Lys Ser Tyr Gln Asn Ser Gln
 50                  55                  60
Ile Ala Ile Pro Gln Lys Arg Thr Val Asn Ser Ile Ser Ser Met Pro
 65                  70                  75                  80
Thr Thr Ala Ser Trp Ser Tyr Ser Gly Ser Asn Ile Arg Ala Asn Val
                 85                  90                  95
Ala Tyr Asp Leu Phe Thr Ala Ala Asn Pro Asn His Val Thr Tyr Ser
                100                 105                 110
Gly Asp Tyr Glu Leu Met Ile Trp Leu Gly Lys Tyr Gly Asp Ile Gly
                115                 120                 125
Pro Ile Gly Ser Ser Gln Gly Thr Val Asn Val Gly Gly Gln Ser Trp
130                 135                 140
Thr Leu Tyr Tyr Gly Tyr Asn Gly Ala Met Gln Val Tyr Ser Phe Val
145                 150                 155                 160
Ala Gln Thr Asn Thr Thr Asn Tyr Ser Gly Asp Val Lys Asn Phe Phe
                165                 170                 175
Asn Tyr Leu Arg Asp Asn Lys Gly Tyr Asn Ala Ala Gly Gln Tyr Val
                180                 185                 190
Leu Ser Tyr Gln Phe Gly Thr Glu Pro Phe Thr Gly Ser Gly Thr Leu
                195                 200                 205
Asn Val Ala Ser Trp Thr Ala Ser Ile Asn
                210                 215

<210> SEQ ID NO 2
<211> LENGTH: 702
<212> TYPE: DNA
<213> ORGANISM: Trichoderma reesei

<400> SEQUENCE: 2
atgaagttcc ttcaagtcct ccctgccctc ataccggccg ccctggccca aaccagctgt     60
gaccagtggg caaccttcac tggcaacggc tacacagtca gcaacaacct tgggggagca    120
tcagccggct ctggatttgg ctgcgtgacg gcggtatcgc tcagcggcgg ggcctcctgg    180
cacgcagact ggcagtggtc cggcggccag aacaacgtca gtcgtacca gaactctcag    240 attgccattc cccagaagag gaccgtcaac agcatcagca gcatgcccac cactgccagc    300
tggagctaca gcgggagcaa catccgcgct aatgttgcgt atgacttgtt caccgcagcc    360
aacccgaatc atgtcacgta ctcgggagac tacgaactca tgatctggct tggcaaatac    420
ggcgatattg gccgattgg gtcctcacag ggaacagtca acgtcggtgg ccagagctgg    480
acgctctact atggctacaa cggagccatg caagtctatt cctttgtggc ccagaccaac    540
actaccaact acagcggaga tgtcaagaac ttcttcaatt atctccgaga caataaagga    600
tacaacgctg caggccaata tgttcttagc taccaatttg gtaccgagcc cttcacgggc    660
agtggaactc tgaacgtcgc atcctggacc gcatctatca ac                       702

<210> SEQ ID NO 3
<211> LENGTH: 234
<212> TYPE: PRT
<213> ORGANISM: Trichoderma reesei

<400> SEQUENCE: 3

Met Lys Phe Leu Gln Val Leu Pro Ala Leu Ile Pro Ala Ala Leu Ala
  1               5                  10                  15
Gln Thr Ser Cys Asp Gln Trp Ala Thr Phe Thr Gly Asn Gly Tyr Thr
```

-continued

```
                    20                  25                  30
Val Ser Asn Asn Leu Trp Gly Ala Ser Ala Gly Ser Gly Phe Gly Cys
                35                  40                  45
Val Thr Ala Val Ser Leu Ser Gly Gly Ala Ser Trp His Ala Asp Trp
         50                  55                  60
Gln Trp Ser Gly Gly Gln Asn Asn Val Lys Ser Tyr Gln Asn Ser Gln
 65                  70                  75                  80
Ile Ala Ile Pro Gln Lys Arg Thr Val Asn Ser Ile Ser Ser Met Pro
                 85                  90                  95
Thr Thr Ala Ser Trp Ser Tyr Ser Gly Ser Asn Ile Arg Ala Asn Val
                100                 105                 110
Ala Tyr Asp Leu Phe Thr Ala Ala Asn Pro Asn His Val Thr Tyr Ser
                115                 120                 125
Gly Asp Tyr Glu Leu Met Ile Trp Leu Gly Lys Tyr Gly Asp Ile Gly
        130                 135                 140
Pro Ile Gly Ser Ser Gln Gly Thr Val Asn Val Gly Gly Gln Ser Trp
145                 150                 155                 160
Thr Leu Tyr Tyr Gly Tyr Asn Gly Ala Met Gln Val Tyr Ser Phe Val
                165                 170                 175
Ala Gln Thr Asn Thr Thr Asn Tyr Ser Gly Asp Val Lys Asn Phe Phe
                180                 185                 190
Asn Tyr Leu Arg Asp Asn Lys Gly Tyr Asn Ala Ala Gly Gln Tyr Val
                195                 200                 205
Leu Ser Tyr Gln Phe Gly Thr Glu Pro Phe Thr Gly Ser Gly Thr Leu
        210                 215                 220
Asn Val Ala Ser Trp Thr Ala Ser Ile Asn
225                 230
```

<210> SEQ ID NO 4
<211> LENGTH: 234
<212> TYPE: PRT
<213> ORGANISM: Hypocrea schweinitzii

<400> SEQUENCE: 4

```
Met Lys Phe Leu Gln Val Leu Pro Ala Ile Leu Pro Ala Ala Leu Ala
 1               5                  10                  15
Gln Thr Ser Cys Asp Gln Tyr Ala Thr Phe Ser Gly Asn Gly Tyr Ile
                20                  25                  30
Val Ser Asn Asn Leu Trp Gly Ala Ser Ala Gly Ser Gly Phe Gly Cys
                35                  40                  45
Val Thr Ser Val Ser Leu Asn Gly Ala Ala Ser Trp His Ala Asp Trp
         50                  55                  60
Gln Trp Ser Gly Gly Gln Asn Asn Val Lys Ser Tyr Gln Asn Val Gln
 65                  70                  75                  80
Ile Asn Ile Pro Gln Lys Arg Thr Val Asn Ser Ile Gly Ser Met Pro
                 85                  90                  95
Thr Thr Ala Ser Trp Ser Tyr Ser Gly Ser Asp Ile Arg Ala Asn Val
                100                 105                 110
Ala Tyr Asp Leu Phe Thr Ala Ala Asn Pro Asn His Val Thr Tyr Ser
                115                 120                 125
Gly Asp Tyr Glu Leu Met Ile Trp Leu Gly Lys Tyr Gly Asp Ile Gly
        130                 135                 140
Pro Ile Gly Ser Ser Gln Gly Thr Val Asn Val Gly Gly Gln Thr Trp
145                 150                 155                 160
```

```
Thr Leu Tyr Tyr Gly Tyr Asn Gly Ala Met Gln Val Tyr Ser Phe Val
                165                 170                 175

Ala Gln Ser Asn Thr Thr Ser Tyr Ser Gly Asp Val Lys Asn Phe Phe
            180                 185                 190

Asn Tyr Leu Arg Asp Asn Lys Gly Tyr Asn Ala Gly Gly Gln Tyr Val
            195                 200                 205

Leu Ser Tyr Gln Phe Gly Thr Glu Pro Phe Thr Gly Ser Gly Thr Leu
        210                 215                 220

Asn Val Ala Ser Trp Thr Ala Ser Ile Asn
225                 230
```

```
<210> SEQ ID NO 5
<211> LENGTH: 259
<212> TYPE: PRT
<213> ORGANISM: Aspergillus aculeatus

<400> SEQUENCE: 5
```

```
Met Lys Ala Phe His Leu Leu Ala Ala Leu Ala Gly Ala Ala Val Ala
 1               5                  10                  15

Gln Gln Ala Gln Leu Cys Asp Gln Tyr Ala Thr Tyr Thr Gly Gly Val
             20                  25                  30

Tyr Thr Ile Asn Asn Asn Leu Trp Gly Lys Asp Ala Gly Ser Gly Ser
            35                  40                  45

Gln Cys Thr Thr Val Asn Ser Ala Ser Ser Ala Gly Thr Ser Trp Ser
 50                  55                  60

Thr Lys Trp Asn Trp Ser Gly Gly Glu Asn Ser Val Lys Ser Tyr Ala
65                  70                  75                  80

Asn Ser Gly Leu Thr Phe Asn Lys Lys Leu Val Ser Gln Ile Ser Gln
                85                  90                  95

Ile Pro Thr Thr Ala Arg Trp Ser Tyr Asp Asn Thr Gly Ile Arg Ala
            100                 105                 110

Asp Val Ala Tyr Asp Leu Phe Thr Ala Ala Asp Ile Asn His Val Thr
            115                 120                 125

Trp Ser Gly Asp Tyr Glu Leu Met Ile Trp Leu Ala Arg Tyr Gly Gly
        130                 135                 140

Val Gln Pro Ile Gly Ser Gln Ile Ala Thr Ala Thr Val Asp Gly Gln
145                 150                 155                 160

Thr Trp Glu Leu Trp Tyr Gly Ala Asn Gly Ser Gln Lys Thr Tyr Ser
                165                 170                 175

Phe Val Ala Pro Thr Pro Ile Thr Ser Phe Gln Gly Asp Val Asn Asp
            180                 185                 190

Phe Phe Lys Tyr Leu Thr Gln Asn His Gly Phe Pro Ala Ser Ser Gln
            195                 200                 205

Tyr Leu Ile Thr Leu Gln Phe Gly Thr Glu Pro Phe Thr Gly Gly Pro
        210                 215                 220

Ala Thr Leu Ser Val Ser Asn Trp Ser Ala Ser Val Gln Ala Gly
225                 230                 235                 240

Phe Glu Pro Trp Gln Asn Gly Ala Gly Leu Ala Val Asn Ser Phe Ser
                245                 250                 255

Ser Thr Val
```

```
<210> SEQ ID NO 6
<211> LENGTH: 239
<212> TYPE: PRT
<213> ORGANISM: Aspergillus kawachii (1)
```

```
<400> SEQUENCE: 6

Met Lys Leu Ser Met Thr Leu Ser Leu Phe Ala Ala Thr Ala Met Gly
 1               5                  10                  15

Gln Thr Met Cys Ser Gln Tyr Asp Ser Ala Ser Pro Pro Tyr Ser
                20                  25                  30

Val Asn Gln Asn Leu Trp Gly Glu Tyr Gln Gly Thr Gly Ser Gln Cys
            35                  40                  45

Val Tyr Val Asp Lys Leu Ser Ser Ser Gly Ala Ser Trp His Thr Lys
 50                  55                  60

Trp Thr Trp Ser Gly Gly Glu Gly Thr Val Lys Ser Tyr Ser Asn Ser
 65                  70                  75                  80

Gly Leu Thr Phe Asp Lys Lys Leu Val Ser Asp Val Ser Ser Ile Pro
                85                  90                  95

Thr Ser Val Thr Trp Ser Gln Asp Asp Thr Asn Val Gln Ala Asp Val
                100                 105                 110

Ser Tyr Asp Leu Phe Thr Ala Ala Asn Ala Asp His Ala Thr Ser Ser
            115                 120                 125

Gly Asp Tyr Glu Leu Met Ile Trp Leu Ala Arg Tyr Gly Ser Val Gln
 130                 135                 140

Pro Ile Gly Lys Gln Ile Ala Thr Ala Thr Val Gly Gly Lys Ser Trp
145                  150                 155                 160

Glu Val Trp Tyr Gly Thr Ser Thr Gln Ala Gly Ala Glu Gln Lys Thr
                165                 170                 175

Tyr Ser Phe Val Ala Gly Ser Pro Ile Asn Ser Trp Ser Gly Asp Ile
            180                 185                 190

Lys Asp Phe Phe Asn Tyr Leu Thr Gln Asn Gln Gly Phe Pro Ala Ser
 195                 200                 205

Ser Gln His Leu Ile Thr Leu Gln Cys Gly Thr Glu Pro Phe Thr Gly
                210                 215                 220

Gly Pro Ala Thr Phe Thr Val Asp Asn Trp Thr Ala Ser Val Asn
225                 230                 235

<210> SEQ ID NO 7
<211> LENGTH: 239
<212> TYPE: PRT
<213> ORGANISM: Aspergillus kawachii (2)

<400> SEQUENCE: 7

Met Lys Ala Phe His Leu Leu Ala Ala Leu Ser Gly Ala Ala Val Ala
 1               5                  10                  15

Gln Gln Ala Gln Leu Cys Asp Gln Tyr Ala Thr Tyr Thr Gly Gly Val
                20                  25                  30

Tyr Thr Ile Asn Asn Asn Leu Trp Gly Lys Asp Ala Gly Ser Gly Ser
            35                  40                  45

Gln Cys Thr Thr Val Asn Ser Ala Ser Ser Ala Gly Thr Ser Trp Ser
 50                  55                  60

Thr Lys Trp Asn Trp Ser Gly Gly Glu Asn Ser Val Lys Ser Tyr Ala
 65                  70                  75                  80

Asn Ser Gly Leu Ser Phe Asn Lys Lys Leu Val Ser Gln Ile Ser His
                85                  90                  95

Ile Pro Thr Ala Ala Arg Trp Ser Tyr Asp Asn Thr Cys Ile Arg Arg
                100                 105                 110

Gly Arg Ala Tyr Asp Leu Phe Thr Ala Ala Asp Ile Asn His Val Thr
            115                 120                 125
```

```
Trp Ser Gly Asp Tyr Glu Leu Met Ile Trp Leu Ala Arg Tyr Gly Gly
    130                 135                 140

Val Gln Pro Leu Gly Ser Gln Ile Ala Thr Ala Thr Val Glu Gly Gln
145                 150                 155                 160

Thr Trp Glu Leu Trp Tyr Gly Val Asn Gly Ala Gln Lys Thr Tyr Ser
                165                 170                 175

Phe Val Ala Ala Asn Pro Ile Thr Ser Phe Gln Gly Asp Ile Asn Asp
                180                 185                 190

Phe Phe Lys Tyr Leu Thr Gln Asn His Gly Phe Pro Ala Ser Ser Gln
                195                 200                 205

Tyr Leu Ile Ile Leu Ala Leu Gln Phe Gly Thr Glu Pro Phe Thr Gly
    210                 215                 220

Gly Pro Ala Thr Leu Asn Val Ala Asp Trp Ser Ala Ser Val Gln
225                 230                 235

<210> SEQ ID NO 8
<211> LENGTH: 247
<212> TYPE: PRT
<213> ORGANISM: Aspergillus oryzae

<400> SEQUENCE: 8

Met Lys Leu Ser Leu Ala Leu Ala Thr Leu Val Ala Thr Ala Phe Ser
1               5                   10                  15

Gln Glu Leu Cys Ala Gln Tyr Asp Ser Ala Ser Ser Pro Pro Tyr Ser
                20                  25                  30

Val Asn Asn Asn Leu Trp Gly Gln Asp Ser Gly Thr Gly Phe Thr Ser
                35                  40                  45

Gln Cys Val Tyr Val Asp Asn Leu Ser Ser Ser Gly Ala Ala Trp His
    50                  55                  60

Thr Thr Trp Thr Trp Asn Gly Gly Glu Gly Ser Val Lys Ser Tyr Ser
65                  70                  75                  80

Asn Ser Ala Val Thr Phe Asp Lys Lys Leu Val Ser Asp Val Gln Ser
                85                  90                  95

Ile Pro Thr Asp Val Glu Trp Ser Gln Asp Phe Thr Asn Thr Asn Val
                100                 105                 110

Asn Ala Asp Val Ala Tyr Asp Leu Phe Thr Ala Ala Asp Gln Asn His
            115                 120                 125

Val Thr Tyr Ser Gly Asp Tyr Glu Leu Met Ile Trp Leu Ala Arg Tyr
    130                 135                 140

Gly Thr Ile Gln Pro Ile Gly Thr Gln Ile Asp Thr Ala Thr Val Glu
145                 150                 155                 160

Gly His Thr Trp Glu Leu Trp Phe Thr Tyr Gly Thr Thr Ile Gln Ala
                165                 170                 175

Gly Ala Glu Gln Lys Thr Tyr Ser Phe Val Ser Ala Thr Pro Ile Asn
                180                 185                 190

Thr Phe Gly Gly Asp Ile Lys Lys Phe Phe Asp Tyr Ile Thr Ser Lys
                195                 200                 205

His Ser Phe Pro Ala Ser Ala Gln Tyr Leu Ile Asn Met Gln Phe Gly
    210                 215                 220

Thr Glu Pro Phe Thr Thr Gly Gly Pro Val Thr Phe Thr Val Pro
225                 230                 235                 240

Asn Trp Thr Ala Ser Val Asn
            245

<210> SEQ ID NO 9
```

```
<211> LENGTH: 254
<212> TYPE: PRT
<213> ORGANISM: Humicola grisea

<400> SEQUENCE: 9
```

Met Leu Lys Ser Ala Leu Leu Gly Ala Ala Val Ser Val Gln
1               5                   10                  15

Ser Ala Ser Ile Pro Thr Ile Pro Ala Asn Leu Glu Pro Arg Gln Ile
            20                  25                  30

Arg Ser Leu Cys Glu Leu Tyr Gly Tyr Trp Ser Gly Asn Gly Tyr Glu
        35                  40                  45

Leu Leu Asn Asn Leu Trp Gly Lys Asp Thr Ala Thr Ser Gly Trp Gln
    50                  55                  60

Cys Thr Tyr Leu Asp Gly Thr Asn Asn Gly Gly Ile Gln Trp Ser Thr
65                  70                  75                  80

Ala Trp Glu Trp Gln Gly Ala Pro Asp Asn Val Lys Ser Tyr Pro Tyr
                85                  90                  95

Val Gly Lys Gln Ile Gln Arg Gly Arg Lys Ile Ser Asp Ile Asn Ser
            100                 105                 110

Met Arg Thr Ser Val Ser Trp Thr Tyr Asp Arg Thr Asp Ile Arg Ala
            115                 120                 125

Asn Val Ala Tyr Asp Val Phe Thr Ala Arg Asp Pro Asp His Pro Asn
    130                 135                 140

Trp Gly Gly Asp Tyr Glu Leu Met Ile Trp Leu Ala Arg Tyr Gly Gly
145                 150                 155                 160

Ile Tyr Pro Ile Gly Thr Phe His Ser Gln Val Asn Leu Ala Gly Arg
                165                 170                 175

Thr Trp Asp Leu Trp Thr Gly Tyr Asn Gly Asn Met Arg Val Tyr Ser
            180                 185                 190

Phe Leu Pro Pro Ser Gly Asp Ile Arg Asp Phe Ser Cys Asp Ile Lys
        195                 200                 205

Asp Phe Phe Asn Tyr Leu Glu Arg Asn His Gly Tyr Pro Ala Arg Glu
    210                 215                 220

Gln Asn Leu Ile Val Tyr Gln Val Gly Thr Glu Cys Phe Thr Gly Gly
225                 230                 235                 240

Pro Ala Arg Phe Thr Cys Arg Asp Phe Arg Ala Asp Leu Trp
                245                 250

```
<210> SEQ ID NO 10
<211> LENGTH: 254
<212> TYPE: PRT
<213> ORGANISM: Humicola insolens

<400> SEQUENCE: 10
```

Met Leu Lys Ser Ala Leu Leu Gly Pro Ala Val Ser Val Gln
1               5                   10                  15

Ser Ala Ser Ile Pro Thr Ile Pro Ala Asn Leu Glu Pro Arg Gln Ile
            20                  25                  30

Arg Ser Leu Cys Glu Leu Tyr Gly Tyr Trp Ser Gly Asn Gly Tyr Glu
        35                  40                  45

Leu Leu Asn Asn Leu Trp Gly Lys Asp Thr Ala Thr Ser Gly Trp Gln
    50                  55                  60

Cys Thr Tyr Leu Asp Gly Thr Asn Asn Gly Gly Ile Gln Trp Ser Thr
65                  70                  75                  80

Ala Trp Glu Trp Gln Gly Ala Pro Asp Asn Val Lys Ser Tyr Pro Tyr
                85                  90                  95

Val Gly Lys Gln Ile Gln Arg Gly Arg Lys Ile Ser Asp Ile Asn Ser
            100                 105                 110

Met Arg Thr Ser Val Ser Trp Thr Tyr Asp Arg Thr Asp Ile Arg Ala
            115                 120                 125

Asn Val Ala Tyr Asp Val Phe Thr Ala Arg Asp Pro Asp His Pro Asn
        130                 135                 140

Trp Gly Gly Asp Tyr Glu Leu Met Ile Trp Leu Ala Arg Tyr Gly Gly
145                 150                 155                 160

Ile Tyr Pro Ile Gly Thr Phe His Ser Gln Val Asn Leu Ala Gly Arg
                165                 170                 175

Thr Trp Asp Leu Trp Thr Gly Tyr Asn Gly Asn Met Arg Val Tyr Ser
            180                 185                 190

Phe Leu Pro Pro Ser Gly Asp Ile Arg Asp Phe Ser Cys Asp Ile Lys
        195                 200                 205

Asp Phe Phe Asn Tyr Leu Glu Arg Asn His Gly Tyr Pro Ala Arg Glu
210                 215                 220

Gln Asn Leu Ile Val Tyr Gln Val Gly Thr Glu Cys Phe Thr Gly Gly
225                 230                 235                 240

Pro Ala Arg Phe Thr Cys Arg Asp Phe Arg Ala Asp Leu Trp
                245                 250

<210> SEQ ID NO 11
<211> LENGTH: 247
<212> TYPE: PRT
<213> ORGANISM: Chaetomium brasilliense

<400> SEQUENCE: 11

Met Lys Leu Thr Leu Val Leu Phe Val Ser Leu Ala Ala Ala Thr
1               5                   10                  15

Pro Leu Gly Trp Arg Glu Arg Gln Gln Gln Val Ser Leu Cys Gly Gln
            20                  25                  30

Ser Ser Ser Trp Ser Gly Asn Gly Tyr Gln Leu Asn Asn Asn Leu Trp
        35                  40                  45

Gly Gln Ser Arg Ala Thr Ser Gly Ser Gln Cys Thr Tyr Leu Asp Ser
    50                  55                  60

Ser Ser Asn Ser Gly Ile His Trp His Thr Thr Trp Thr Trp Glu Gly
65                  70                  75                  80

Gly Glu Gly Glu Val Lys Ser Tyr Ala Tyr Ser Gly Arg Gln Val Ser
                85                  90                  95

Thr Gly Leu Thr Ile Ala Ser Ile Asp Ser Met Gln Thr Ser Val Ser
            100                 105                 110

Trp Glu Tyr Asn Thr Thr Asp Ile Gln Ala Asn Val Ala Tyr Asp Ile
        115                 120                 125

Phe Thr Ala Glu Asp Pro Asp His Glu His Ser Ser Gly Asp Tyr Glu
    130                 135                 140

Leu Met Ile Trp Leu Ala Arg Tyr Asn Val Ser Pro Ile Gly Ser
145                 150                 155                 160

Ser Val Ala Thr Ala Thr Val Gly Gly Asp Thr Trp Asp Leu Phe Ala
                165                 170                 175

Gly Ala Asn Gly Asp Met Glu Val Tyr Ser Phe Val Ala Glu Asn Thr
            180                 185                 190

Met Asn Ser Phe Ser Gly Asp Val Lys Asp Phe Asp Tyr Leu Glu
        195                 200                 205

Gln Asn Val Gly Phe Pro Val Asp Asp Gln Tyr Leu Leu Val Phe Glu

```
            210                 215                 220
Leu Gly Ser Glu Ala Phe Thr Gly Gly Pro Ala Thr Leu Ser Val Ser
225                 230                 235                 240

Gln Phe Ser Ala Asn Ile Ala
                245

<210> SEQ ID NO 12
<211> LENGTH: 238
<212> TYPE: PRT
<213> ORGANISM: Fusarium equiseti

<400> SEQUENCE: 12

Met Lys Ser Thr Leu Leu Ala Gly Ala Phe Ala Pro Leu Ala Phe
  1               5                  10                  15

Ala Lys Asp Leu Cys Glu Gln Tyr Gly Tyr Leu Ser Ser Asp Gly Tyr
                 20                  25                  30

Ser Leu Asn Asn Val Trp Gly Lys Asp Ser Gly Thr Gly Asp Gln
             35                  40                  45

Cys Thr His Val Asn Trp Asn Ala Asn Gly Ala Gly Trp Asp Val
         50                  55                  60

Glu Trp Asn Trp Ser Gly Gly Lys Asp Asn Val Lys Ser Tyr Pro Asn
65                  70                  75                  80

Ser Ala Leu Leu Ile Gly Glu Asp Lys Lys Thr Ile Ser Ser Ile Thr
                 85                  90                  95

Asn Met Gln Ser Thr Ala Glu Trp Lys Tyr Ser Gly Asp Asn Leu Arg
            100                 105                 110

Ala Asp Val Ala Tyr Asp Leu Phe Thr Ala Ala Asp Pro Asn His Glu
            115                 120                 125

Thr Ser Ser Gly Glu Tyr Glu Leu Met Val Trp Leu Ala Arg Ile Gly
            130                 135                 140

Gly Val Gln Pro Ile Gly Ser Leu Gln Thr Ser Val Thr Ile Glu Gly
145                 150                 155                 160

His Thr Trp Glu Leu Trp Val Gly Met Asn Gly Ser Met Lys Val Phe
                165                 170                 175

Ser Phe Val Ala Pro Thr Pro Val Asn Asn Phe Asn Ala Asp Ile Lys
                180                 185                 190

Gln Phe Trp Asp Tyr Leu Thr Lys Ser Gln Asn Phe Pro Ala Asp Asn
            195                 200                 205

Gln Tyr Leu Leu Thr Phe Gln Phe Gly Thr Glu Pro Phe Thr Gly Asp
            210                 215                 220

Asn Ala Lys Phe Thr Val Thr Asn Phe Asn Ala His Leu Lys
225                 230                 235

<210> SEQ ID NO 13
<211> LENGTH: 244
<212> TYPE: PRT
<213> ORGANISM: Fusarium javanicum (1)

<400> SEQUENCE: 13

Met Lys Ser Ala Ile Val Ala Ala Leu Ala Gly Leu Ala Ala Ala Ser
  1               5                  10                  15

Pro Thr Arg Leu Ile Pro Arg Gly Gln Phe Cys Gly Gln Trp Asp Ser
                 20                  25                  30

Glu Thr Ala Gly Ala Tyr Thr Ile Tyr Asn Asn Leu Trp Gly Lys Asp
             35                  40                  45

Asn Ala Glu Ser Gly Glu Gln Cys Thr Thr Asn Ser Gly Glu Gln Ser
```

```
                50                  55                  60
Asp Gly Ser Ile Ala Trp Ser Val Glu Trp Ser Trp Thr Gly Gly Gln
 65                  70                  75                  80

Gly Gln Val Lys Ser Tyr Pro Asn Ala Val Val Glu Ile Glu Lys Lys
                     85                  90                  95

Thr Leu Gly Glu Val Ser Ser Ile Pro Ser Ala Trp Asp Trp Thr Tyr
                    100                 105                 110

Thr Gly Asn Gly Ile Ile Ala Asn Val Ala Tyr Asp Leu Phe Thr Ser
                    115                 120                 125

Ser Thr Glu Ser Gly Asp Ala Glu Tyr Glu Phe Met Ile Trp Leu Ser
            130                 135                 140

Ala Leu Gly Gly Ala Gly Pro Ile Ser Asn Asp Gly Ser Pro Val Ala
145                 150                 155                 160

Thr Ala Glu Leu Ala Gly Thr Ser Trp Lys Leu Tyr Gln Gly Lys Asn
                    165                 170                 175

Asn Gln Met Thr Val Phe Ser Phe Val Ala Glu Ser Asp Val Asn Asn
                180                 185                 190

Phe Cys Gly Asp Leu Ala Asp Phe Thr Asp Tyr Leu Val Asp Asn His
                195                 200                 205

Gly Val Ser Ser Gln Ile Leu Gln Ser Val Gly Ala Gly Thr Glu
            210                 215                 220

Pro Phe Glu Gly Thr Asn Ala Val Phe Thr Thr Asn Asn Tyr His Ala
225                 230                 235                 240

Asp Val Glu Tyr

<210> SEQ ID NO 14
<211> LENGTH: 250
<212> TYPE: PRT
<213> ORGANISM: Fusarium javanicum (2)

<400> SEQUENCE: 14

Met Lys Phe Phe Gly Val Val Ser Ala Ser Leu Ala Ala Thr Ala Val
 1               5                  10                  15

Ala Thr Pro Thr Thr Pro Thr Glu Thr Ile Glu Lys Arg Asp Thr Thr
                 20                  25                  30

Trp Cys Asp Ala Phe Gly Ser Leu Ala Thr Ser Gly Tyr Thr Val Tyr
                 35                  40                  45

His Asn Asn Trp Gly Lys Gly Asp Ala Thr Ser Gly Ser Gln Cys Thr
 50                  55                  60

Thr Phe Thr Ser Val Ser Asn Asn Asn Phe Val Trp Ser Thr Ser Trp
 65                  70                  75                  80

Thr Trp Ala Gly Gly Ala Gly Lys Val Lys Ser Tyr Ser Asn Val Ala
                 85                  90                  95

Leu Glu Lys Ile Asn Lys Lys Ile Ser Asp Ile Lys Ser Val Ser Thr
                100                 105                 110

Arg Trp Ile Trp Arg Tyr Thr Gly Thr Lys Met Ile Ala Asn Val Ser
                115                 120                 125

Tyr Asp Leu Trp Phe Ala Pro Thr Ala Ser Ser Asn Asn Ala Tyr Glu
            130                 135                 140

Ile Met Ile Trp Val Gly Ala Tyr Gly Gly Ala Leu Pro Ile Ser Thr
145                 150                 155                 160

Pro Gly Lys Gly Val Ile Asp Arg Pro Thr Leu Ala Gly Ile Pro Trp
                165                 170                 175

Asp Val Tyr Lys Gly Pro Asn Gly Asp Val Thr Val Ile Ser Phe Val
```

```
            180             185             190
Ala Ser Ser Asn Gln Gly Asn Phe Gln Ala Asp Leu Lys Glu Phe Leu
        195             200             205

Asn Tyr Leu Thr Ser Lys Gln Gly Leu Pro Ser Asn Tyr Val Ala Thr
        210             215             220

Ser Phe Gln Ala Gly Thr Glu Pro Phe Glu Gly Thr Asn Ala Val Leu
225             230             235             240

Lys Thr Ser Ala Tyr Thr Ile Ser Val Asn
                245             250

<210> SEQ ID NO 15
<211> LENGTH: 238
<212> TYPE: PRT
<213> ORGANISM: Gliocladium roseum (1)

<400> SEQUENCE: 15

Met Lys Ala Asn Ile Val Ile Leu Ser Leu Phe Ala Pro Leu Ala Ala
1               5                   10                  15

Val Ala Gln Thr Leu Cys Gly Gln Tyr Ser Ser Asn Thr Gln Gly Gly
            20                  25                  30

Tyr Ile Phe Asn Asn Asn Met Trp Gly Met Gly Ser Gly Ser Gly Ser
        35                  40                  45

Gln Cys Thr Tyr Val Asp Lys Val Trp Ala Glu Gly Val Ala Trp His
    50                  55                  60

Thr Asp Trp Ser Trp Ser Gly Gly Asp Asn Asn Val Lys Ser Tyr Pro
65                  70                  75                  80

Tyr Ser Gly Arg Glu Leu Gly Thr Lys Arg Ile Val Ser Ser Ile Lys
                85                  90                  95

Ser Ile Ser Ser Gly Ala Asp Trp Asp Tyr Thr Gly Ser Asn Leu Arg
            100                 105                 110

Ala Asn Ala Ala Tyr Asp Ile Phe Thr Ser Ala Asn Pro Asn His Ala
        115                 120                 125

Thr Ser Ser Gly Asp Tyr Glu Val Met Ile Trp Leu Ala Asn Leu Gly
    130                 135                 140

Gly Leu Thr Pro Ile Gly Ser Pro Ile Gly Thr Val Lys Ala Ala Gly
145                 150                 155                 160

Arg Asp Trp Glu Leu Trp Asp Gly Tyr Asn Gly Ala Met Arg Val Tyr
                165                 170                 175

Ser Phe Val Ala Pro Ser Gln Leu Asn Ser Phe Asp Gly Glu Ile Met
            180                 185                 190

Asp Phe Phe Tyr Val Val Lys Asp Met Arg Gly Phe Pro Ala Asp Ser
        195                 200                 205

Gln His Leu Leu Thr Val Gln Phe Gly Thr Glu Pro Ile Ser Gly Ser
    210                 215                 220

Gly Ala Lys Phe Ser Val Ser His Trp Ser Ala Lys Leu Gly
225                 230                 235

<210> SEQ ID NO 16
<211> LENGTH: 348
<212> TYPE: PRT
<213> ORGANISM: Gliocladium roseum (2)

<400> SEQUENCE: 16

Met Lys Ser Ile Ile Ser Phe Phe Gly Leu Ala Thr Leu Val Ala Ala
1               5                   10                  15

Ala Pro Ser Gln Asn Pro Thr Arg Thr Gln Pro Leu Glu Lys Arg Ala
```

```
                    20                  25                  30
Thr Thr Leu Cys Gly Gln Trp Asp Ser Val Glu Thr Gly Gly Tyr Thr
                35                  40                  45

Ile Tyr Asn Asn Leu Trp Gly Gln Asp Asn Gly Ser Gly Ser Gln Cys
 50                  55                  60

Leu Thr Val Glu Gly Val Thr Asp Gly Leu Ala Ala Trp Ser Ser Thr
65                  70                  75                  80

Trp Ser Trp Ser Gly Gly Ser Ser Val Lys Ser Tyr Ser Asn Ala
                85                  90                  95

Val Leu Ser Ala Glu Ala Ala Arg Ile Ser Ala Ile Ser Ser Ile Pro
                100                 105                 110

Ser Lys Trp Glu Trp Ser Tyr Thr Gly Thr Asp Ile Val Ala Asn Val
                115                 120                 125

Ala Tyr Asp Leu Phe Ser Asn Thr Asp Cys Gly Asp Thr Pro Glu Tyr
                130                 135                 140

Glu Ile Met Ile Trp Leu Ser Ala Leu Gly Gly Ala Gly Pro Ile Ser
145                 150                 155                 160

Ser Thr Gly Ser Ser Ile Ala Thr Val Thr Ile Ala Gly Ala Ser Trp
                165                 170                 175

Asn Leu Trp Gln Gly Gln Asn Asn Gln Met Ala Val Phe Ser Phe Val
                180                 185                 190

Ala Glu Ser Asp Gln Lys Ser Phe Ser Gly Asp Leu Asn Asp Phe Ile
                195                 200                 205

Gln Tyr Leu Val Asp Ser Gly Tyr Ser Gly Ser Gln Cys Leu Tyr
                210                 215                 220

Ser Ile Gly Ala Gly Thr Glu Pro Phe Thr Gly Thr Asp Ala Glu Phe
225                 230                 235                 240

Ile Thr Thr Gly Tyr Ser Val Ser Val Ser Ala Gly Asp Ser Gly Cys
                245                 250                 255

Asp Glu Thr Thr Thr Ser Ser Gln Ala Gln Ser Ser Thr Val Glu Thr
                260                 265                 270

Ser Thr Ala Thr Gln Pro Gln Ser Ser Thr Val Val Pro Thr Val
                275                 280                 285

Thr Leu Ser Gln Pro Ser Asn Glu Ser Thr Thr Pro Val Gln Ser
                290                 295                 300

Gln Pro Ser Ser Val Glu Thr Thr Pro Thr Ala Gln Pro Gln Ser Ser
305                 310                 315                 320

Ser Val Gln Thr Thr Thr Thr Ala Gln Ala Gln Pro Thr Ser Gly Thr
                325                 330                 335

Gly Cys Ser Arg Arg Arg Lys Arg Arg Ala Val Val
                340                 345

<210> SEQ ID NO 17
<211> LENGTH: 236
<212> TYPE: PRT
<213> ORGANISM: Gliocladium roseum (3)

<400> SEQUENCE: 17

Met Lys Phe Gln Leu Leu Ser Leu Thr Ala Phe Ala Pro Leu Ser Leu
 1               5                   10                  15

Ala Ala Leu Cys Gly Gln Tyr Gln Ser Gln Ser Gln Gly Gly Tyr Ile
                20                  25                  30

Phe Asn Asn Asn Lys Trp Gly Gln Gly Ser Gly Ser Gly Ser Gln Cys
                35                  40                  45
```

-continued

```
Leu Thr Ile Asp Lys Thr Trp Asp Ser Asn Val Ala Phe His Ala Asp
    50                  55                  60

Trp Ser Trp Ser Gly Thr Asn Asn Val Lys Ser Tyr Pro Asn Ala
 65              70                  75                  80

Gly Leu Glu Phe Ser Arg Gly Lys Lys Val Ser Ser Ile Gly Thr Ile
                85                  90                  95

Asn Gly Gly Ala Asp Trp Asp Tyr Ser Gly Ser Asn Ile Arg Ala Asn
                100                 105                 110

Val Ala Tyr Asp Ile Phe Thr Ser Ala Asp Pro Asn His Val Thr Ser
            115                 120                 125

Ser Gly Asp Tyr Glu Leu Met Ile Trp Leu Gly Lys Leu Gly Asp Ile
    130                 135                 140

Tyr Pro Ile Gly Asn Ser Ile Gly Arg Val Lys Ala Ala Asn Arg Glu
145                 150                 155                 160

Trp Asp Leu His Val Gly Tyr Asn Gly Ala Met Lys Val Phe Ser Phe
                165                 170                 175

Val Ala Pro Ser Pro Val Thr Arg Phe Asp Gly Asn Ile Met Asp Phe
                180                 185                 190

Phe Tyr Val Met Arg Asp Met Gln Gly Tyr Pro Met Asp Lys Gln Tyr
            195                 200                 205

Leu Leu Ser Leu Gln Phe Gly Thr Glu Pro Phe Thr Gly Ser Asn Ala
        210                 215                 220

Lys Phe Ser Cys Trp Tyr Phe Gly Ala Lys Ile Lys
225                 230                 235

<210> SEQ ID NO 18
<211> LENGTH: 237
<212> TYPE: PRT
<213> ORGANISM: Gliocladium roseum (4)

<400> SEQUENCE: 18

Met Lys Thr Gly Ile Ala Tyr Leu Ala Ala Val Leu Pro Leu Ala Met
  1               5                  10                  15

Ala Glu Ser Leu Cys Asp Gln Tyr Ala Tyr Leu Ser Arg Asp Gly Tyr
                20                  25                  30

Asn Phe Asn Asn Asn Glu Trp Gly Ala Ala Thr Gly Thr Gly Asp Gln
            35                  40                  45

Cys Thr Tyr Val Asp Ser Thr Ser Ser Gly Gly Val Ser Trp His Ser
    50                  55                  60

Asp Trp Thr Trp Ser Gly Ser Glu Ser Glu Ile Lys Ser Tyr Pro Tyr
 65              70                  75                  80

Ser Gly Leu Asp Leu Pro Glu Lys Lys Ile Val Thr Ser Ile Gly Ser
                85                  90                  95

Ile Ser Thr Gly Ala Glu Trp Ser Tyr Ser Gly Ser Asp Ile Arg Ala
                100                 105                 110

Asp Val Ala Tyr Asp Thr Phe Thr Ala Ala Asp Pro Asn His Ala Thr
            115                 120                 125

Ser Ser Gly Asp Tyr Glu Val Met Ile Trp Leu Ala Asn Leu Gly Gly
    130                 135                 140

Leu Thr Pro Ile Gly Ser Pro Ile Gly Thr Val Lys Ala Ala Gly Arg
145                 150                 155                 160

Asp Trp Glu Leu Trp Asp Gly Tyr Asn Gly Ala Met Arg Val Tyr Ser
                165                 170                 175

Phe Val Ala Pro Ser Gln Leu Asn Ser Phe Asp Gly Glu Ile Met Asp
                180                 185                 190
```

-continued

```
Phe Phe Tyr Val Lys Asp Met Arg Gly Phe Pro Ala Asp Ser Gln
            195                 200                 205

His Leu Leu Thr Val Gln Phe Gly Thr Glu Pro Ile Ser Gly Ser Gly
            210                 215                 220

Ala Lys Phe Ser Val Ser His Trp Ser Ala Lys Leu Gly
225                 230                 235

<210> SEQ ID NO 19
<211> LENGTH: 237
<212> TYPE: PRT
<213> ORGANISM: Memnoniella echinata

<400> SEQUENCE: 19

Met Lys Val Ala Ala Leu Leu Val Ala Leu Ser Pro Leu Ala Phe Ala
1               5                   10                  15

Gln Ser Leu Cys Asp Gln Tyr Ser Tyr Tyr Ser Ser Asn Gly Tyr Glu
            20                  25                  30

Phe Asn Asn Met Trp Gly Arg Asn Ser Gly Gln Gly Asn Gln Cys
            35                  40                  45

Thr Tyr Val Asp Tyr Ser Ser Pro Asn Gly Val Gly Trp Arg Val Asn
        50                  55                  60

Trp Asn Trp Ser Gly Gly Asp Asn Val Lys Ser Tyr Pro Tyr Ser
65                  70                  75                  80

Gly Arg Gln Leu Pro Thr Lys Arg Ile Val Ser Trp Ile Gly Ser Leu
                85                  90                  95

Pro Thr Thr Val Ser Trp Asn Tyr Gln Gly Asn Asn Leu Arg Ala Asn
            100                 105                 110

Val Ala Tyr Asp Leu Phe Thr Ala Ala Asn Pro Asn His Pro Asn Ser
            115                 120                 125

Ser Gly Asp Tyr Glu Leu Met Ile Trp Leu Gly Arg Leu Gly Asn Val
            130                 135                 140

Tyr Pro Ile Gly Asn Gln Val Ala Thr Val Asn Ile Ala Gly Gln Gln
145                 150                 155                 160

Trp Asn Leu Tyr Tyr Gly Tyr Asn Gly Ala Met Gln Val Tyr Ser Phe
                165                 170                 175

Val Ser Pro Asn Gln Leu Asn Tyr Phe Ser Gly Asn Val Lys Asp Phe
            180                 185                 190

Phe Thr Tyr Leu Gln Tyr Asn Arg Ala Tyr Pro Ala Asp Ser Gln Tyr
            195                 200                 205

Leu Ile Thr Tyr Gln Phe Gly Thr Glu Pro Phe Thr Gly Gln Asn Ala
            210                 215                 220

Val Phe Thr Val Ser Asn Trp Ser Ala Gln Gln Asn Asn
225                 230                 235

<210> SEQ ID NO 20
<211> LENGTH: 246
<212> TYPE: PRT
<213> ORGANISM: Emericella desertoru

<400> SEQUENCE: 20

Met Lys Leu Leu Ala Leu Ser Leu Val Ser Leu Ala Ser Ala Ala Ser
1               5                   10                  15

Ala Ala Ser Ile Leu Ser Asn Thr Phe Thr Arg Arg Ser Asp Phe Cys
            20                  25                  30

Gly Gln Trp Asp Thr Ala Thr Val Gly Asn Phe Ile Val Tyr Asn Asn
            35                  40                  45
```

-continued

Leu Trp Gly Gln Asp Asn Ala Asp Ser Gly Ser Gln Thr Gly Val Asp
    50                  55                  60

Ser Ala Asn Gly Asn Ser Ile Ser Trp His Thr Thr Trp Ser Trp Ser
65                  70                  75                  80

Gly Gly Ser Ser Ser Val Lys Ser Tyr Ala Asn Ala Ala Tyr Gln Phe
                85                  90                  95

Thr Ser Thr Lys Leu Asn Ser Leu Ser Ser Ile Pro Thr Ser Trp Lys
            100                 105                 110

Trp Gln Tyr Ser Thr Thr Asp Ile Val Ala Asn Val Ala Tyr Asp Leu
        115                 120                 125

Phe Thr Ser Ser Ala Gly Gly Asp Ser Glu Tyr Glu Ile Met Ile
130                 135                 140

Trp Leu Ala Ala Leu Gly Gly Ala Gly Pro Ile Ser Ser Thr Gly Ser
145                 150                 155                 160

Ser Ile Ala Thr Val Thr Leu Gly Gly Val Thr Trp Ser Leu Tyr Ser
                165                 170                 175

Gly Pro Asn Gly Ser Met Gln Val Tyr Ser Phe Val Ala Ser Ser Thr
            180                 185                 190

Thr Glu Ser Phe Ser Ala Asp Leu Met Asp Phe Ile Asn Tyr Leu Ala
        195                 200                 205

Glu Asn Gln Gly Leu Ser Ser Ser Gln Tyr Leu Thr His Val Gln Ala
    210                 215                 220

Gly Thr Glu Pro Phe Thr Gly Thr Asp Ala Thr Leu Thr Val Ser Ser
225                 230                 235                 240

Tyr Ser Val Ser Val Ser
                245

<210> SEQ ID NO 21
<211> LENGTH: 371
<212> TYPE: PRT
<213> ORGANISM: Actinomycete 11AG8

<400> SEQUENCE: 21

Met Arg Ser His Pro Arg Ser Ala Thr Met Thr Val Leu Val Val Leu
1               5                   10                  15

Ala Ser Leu Gly Ala Leu Leu Thr Ala Ala Pro Ala Gln Ala Asn
                20                  25                  30

Gln Gln Ile Cys Asp Arg Tyr Gly Thr Thr Ile Gln Asp Arg Tyr
            35                  40                  45

Val Val Gln Asn Asn Arg Trp Gly Thr Ser Ala Thr Gln Cys Ile Asn
50                  55                  60

Val Thr Gly Asn Gly Phe Glu Ile Thr Gln Ala Asp Gly Ser Val Pro
65                  70                  75                  80

Thr Asn Gly Ala Pro Lys Ser Tyr Pro Ser Val Tyr Asp Gly Cys His
                85                  90                  95

Tyr Gly Asn Cys Ala Pro Arg Thr Thr Leu Pro Met Arg Ile Ser Ser
            100                 105                 110

Ile Gly Ser Ala Pro Ser Ser Val Ser Tyr Arg Tyr Thr Gly Asn Gly
        115                 120                 125

Val Tyr Asn Ala Ala Tyr Asp Ile Trp Leu Asp Pro Thr Pro Arg Thr
    130                 135                 140

Asn Gly Val Asn Arg Thr Glu Ile Met Ile Trp Phe Asn Arg Val Gly
145                 150                 155                 160

Pro Val Gln Pro Ile Gly Ser Pro Val Gly Thr Ala His Val Gly Gly

```
                    165                 170                 175
Arg Ser Trp Glu Val Trp Thr Gly Ser Asn Gly Ser Asn Asp Val Ile
            180                 185                 190

Ser Phe Leu Ala Pro Ser Ala Ile Ser Ser Trp Ser Phe Asp Val Lys
            195                 200                 205

Asp Phe Val Asp Gln Ala Val Ser His Gly Leu Ala Thr Pro Asp Trp
            210                 215                 220

Tyr Leu Thr Ser Ile Gln Ala Gly Phe Glu Pro Trp Glu Gly Gly Thr
225                 230                 235                 240

Gly Leu Ala Val Asn Ser Phe Ser Ser Ala Val Asn Ala Gly Gly Gly
                245                 250                 255

Asn Gly Gly Thr Pro Gly Thr Pro Ala Ala Cys Gln Val Ser Tyr Ser
            260                 265                 270

Thr His Thr Trp Pro Gly Gly Phe Thr Val Asp Thr Ile Thr Asn
            275                 280                 285

Thr Gly Ser Thr Pro Val Asp Gly Trp Glu Leu Asp Phe Thr Leu Pro
            290                 295                 300

Ala Gly His Thr Val Thr Ser Ala Trp Asn Ala Leu Ile Ser Pro Ala
305                 310                 315                 320

Ser Gly Ala Val Thr Ala Arg Ser Thr Gly Ser Asn Gly Arg Ile Ala
                325                 330                 335

Ala Asn Gly Gly Thr Gln Ser Phe Gly Phe Gln Gly Thr Ser Ser Gly
            340                 345                 350

Thr Gly Phe Asn Ala Pro Ala Gly Gly Arg Leu Asn Gly Thr Ser Cys
            355                 360                 365

Thr Val Arg
    370

<210> SEQ ID NO 22
<211> LENGTH: 381
<212> TYPE: PRT
<213> ORGANISM: Streptomyces lividans CelB

<400> SEQUENCE: 22

Met Arg Thr Leu Arg Pro Gln Ala Arg Ala Pro Arg Gly Leu Leu Ala
 1               5                  10                  15

Ala Leu Gly Ala Val Leu Ala Ala Phe Ala Leu Val Ser Ser Leu Val
            20                  25                  30

Thr Ala Ala Ala Pro Ala Gln Ala Asp Thr Thr Ile Cys Glu Pro Phe
            35                  40                  45

Gly Thr Thr Thr Ile Gln Gly Arg Tyr Val Val Gln Asn Asn Arg Trp
        50                  55                  60

Gly Ser Thr Ala Pro Gln Cys Val Thr Ala Thr Asp Thr Gly Phe Arg
65                  70                  75                  80

Val Thr Gln Ala Asp Gly Ser Ala Pro Thr Asn Gly Ala Pro Lys Ser
                85                  90                  95

Tyr Pro Ser Val Phe Asn Gly Cys His Tyr Thr Asn Cys Ser Pro Gly
            100                 105                 110

Thr Asp Leu Pro Val Arg Leu Asp Thr Val Ser Ala Ala Pro Ser Ser
            115                 120                 125

Ile Ser Tyr Gly Phe Val Asp Gly Ala Val Tyr Asn Ala Ser Tyr Asp
        130                 135                 140

Ile Trp Leu Asp Pro Thr Ala Arg Thr Asp Gly Val Asn Gln Thr Glu
145                 150                 155                 160
```

-continued

```
Ile Met Ile Trp Phe Asn Arg Val Gly Pro Ile Gln Pro Ile Gly Ser
                165                 170                 175

Pro Val Gly Thr Ala Ser Val Gly Gly Arg Thr Trp Glu Val Trp Ser
            180                 185                 190

Gly Gly Asn Gly Ser Asn Asp Val Leu Ser Phe Val Ala Pro Ser Ala
        195                 200                 205

Ile Ser Gly Trp Ser Phe Asp Val Met Asp Phe Val Arg Ala Thr Val
    210                 215                 220

Ala Arg Gly Leu Ala Glu Asn Asp Trp Tyr Leu Thr Ser Val Gln Ala
225                 230                 235                 240

Gly Phe Glu Pro Trp Gln Asn Gly Ala Gly Leu Ala Val Asn Ser Phe
                245                 250                 255

Ser Ser Thr Val Glu Thr Gly Thr Pro Gly Gly Thr Asp Pro Gly Asp
            260                 265                 270

Pro Gly Gly Pro Ser Ala Cys Ala Val Ser Tyr Gly Thr Asn Val Trp
        275                 280                 285

Gln Asp Gly Phe Thr Ala Asp Val Thr Val Thr Asn Thr Gly Thr Ala
    290                 295                 300

Pro Val Asp Gly Trp Gln Leu Ala Phe Thr Leu Pro Ser Gly Gln Arg
305                 310                 315                 320

Ile Thr Asn Ala Trp Asn Ala Ser Leu Thr Pro Ser Ser Gly Ser Val
                325                 330                 335

Thr Ala Thr Gly Ala Ser His Asn Ala Arg Ile Ala Pro Gly Gly Ser
            340                 345                 350

Leu Ser Phe Gly Phe Gln Gly Thr Tyr Gly Gly Ala Phe Ala Glu Pro
        355                 360                 365

Thr Gly Phe Arg Leu Asn Gly Thr Ala Cys Thr Thr Val
    370                 375                 380

<210> SEQ ID NO 23
<211> LENGTH: 260
<212> TYPE: PRT
<213> ORGANISM: Rhodothermus marinus

<400> SEQUENCE: 23

Met Asn Val Met Arg Ala Val Leu Val Leu Ser Leu Leu Leu Leu Phe
1               5                   10                  15

Gly Cys Asp Trp Leu Phe Pro Asp Gly Asp Asn Gly Lys Glu Pro Glu
            20                  25                  30

Pro Glu Pro Glu Pro Thr Val Glu Leu Cys Gly Arg Trp Asp Ala Arg
        35                  40                  45

Asp Val Ala Gly Gly Arg Tyr Arg Val Ile Asn Asn Val Trp Gly Ala
    50                  55                  60

Glu Thr Ala Gln Cys Ile Glu Val Gly Leu Glu Thr Gly Asn Phe Thr
65                  70                  75                  80

Ile Thr Arg Ala Asp His Asp Asn Gly Asn Asn Val Ala Ala Tyr Pro
                85                  90                  95

Ala Ile Tyr Phe Gly Cys His Trp Ala Pro Ala Arg Ala Ile Arg Asp
            100                 105                 110

Cys Ala Ala Arg Ala Gly Ala Val Arg Arg Ala His Glu Leu Asp Val
        115                 120                 125

Thr Pro Ile Thr Thr Gly Arg Trp Asn Ala Ala Tyr Asp Ile Trp Phe
    130                 135                 140

Ser Pro Val Thr Asn Ser Gly Asn Gly Tyr Ser Gly Gly Ala Glu Leu
145                 150                 155                 160
```

-continued

```
Met Ile Trp Leu Asn Trp Asn Gly Gly Val Met Pro Gly Gly Ser Arg
            165                 170                 175

Val Ala Thr Val Glu Leu Ala Gly Ala Thr Trp Glu Val Trp Tyr Ala
        180                 185                 190

Asp Trp Asp Trp Asn Tyr Ile Ala Tyr Arg Arg Thr Thr Pro Thr Thr
            195                 200                 205

Ser Val Ser Glu Leu Asp Leu Lys Ala Phe Ile Asp Asp Ala Val Ala
    210                 215                 220

Arg Gly Tyr Ile Arg Pro Glu Trp Tyr Leu His Ala Val Glu Thr Gly
225                 230                 235                 240

Phe Glu Leu Trp Glu Gly Gly Ala Gly Leu Arg Thr Ala Asp Phe Ser
                245                 250                 255

Val Thr Val Gln
            260

<210> SEQ ID NO 24
<211> LENGTH: 264
<212> TYPE: PRT
<213> ORGANISM: Erwinia carotovara

<400> SEQUENCE: 24

Met Gln Thr Val Asn Thr Gln Pro His Arg Ile Phe Arg Val Leu Leu
1               5                   10                  15

Pro Ala Val Phe Ser Ser Leu Leu Ser Ser Leu Thr Val Ser Ala
            20                  25                  30

Ala Ser Ser Ser Asn Asp Ala Asp Lys Leu Tyr Phe Gly Asn Asn Lys
        35                  40                  45

Tyr Tyr Leu Phe Asn Asn Val Trp Gly Lys Asp Glu Ile Lys Gly Trp
    50                  55                  60

Gln Gln Thr Ile Phe Tyr Asn Ser Pro Ile Ser Met Gly Trp Asn Trp
65                  70                  75                  80

His Trp Pro Ser Ser Thr His Ser Val Lys Ala Tyr Pro Ser Leu Val
                85                  90                  95

Ser Gly Trp His Trp Thr Ala Gly Tyr Thr Glu Asn Ser Gly Leu Pro
            100                 105                 110

Ile Gln Leu Ser Ser Asn Lys Ser Ile Thr Ser Asn Val Thr Tyr Ser
        115                 120                 125

Ile Lys Ala Thr Gly Thr Tyr Asn Ala Ala Tyr Asp Ile Trp Phe His
    130                 135                 140

Thr Thr Asp Lys Ala Asn Trp Asp Ser Ser Pro Thr Asp Glu Leu Met
145                 150                 155                 160

Ile Trp Leu Asn Asp Thr Asn Ala Gly Pro Ala Gly Asp Tyr Ile Glu
                165                 170                 175

Thr Val Phe Leu Gly Asp Ser Ser Trp Asn Val Phe Lys Gly Trp Ile
            180                 185                 190

Asn Ala Asp Asn Gly Gly Gly Trp Asn Val Phe Ser Phe Val His Thr
        195                 200                 205

Ser Gly Thr Asn Ser Ala Ser Leu Asn Ile Arg His Phe Thr Asp Tyr
    210                 215                 220

Leu Val Gln Thr Lys Gln Trp Met Ser Asp Glu Lys Tyr Ile Ser Ser
225                 230                 235                 240

Val Glu Phe Gly Thr Glu Ile Phe Gly Gly Asp Gly Gln Ile Asp Ile
                245                 250                 255

Thr Glu Trp Arg Val Asp Val Lys
```

```
<210> SEQ ID NO 25
<211> LENGTH: 5
<212> TYPE: PRT
<213> ORGANISM: Artificial Sequence
<220> FEATURE:
<221> NAME/KEY: VARIANT
<222> LOCATION: (1)...(5)
<223> OTHER INFORMATION: Xaa = Leu, Phe, Lys or Ile
<223> OTHER INFORMATION: EGIII-like cellulase amino acid string

<400> SEQUENCE: 25

Asn Asn Xaa Trp Gly
 1               5

<210> SEQ ID NO 26
<211> LENGTH: 5
<212> TYPE: PRT
<213> ORGANISM: Artificial Sequence
<220> FEATURE:
<221> NAME/KEY: VARIANT
<222> LOCATION: (1)...(5)
<223> OTHER INFORMATION: Xaa = Leu, Phe or Ile
<223> OTHER INFORMATION: EGIII-like cellulase amino acid string

<400> SEQUENCE: 26

Glu Xaa Met Ile Trp
 1               5

<210> SEQ ID NO 27
<211> LENGTH: 6
<212> TYPE: PRT
<213> ORGANISM: Artificial Sequence
<220> FEATURE:
<223> OTHER INFORMATION: EGIII-like cellulase amino acid string

<400> SEQUENCE: 27

Gly Thr Glu Pro Phe Thr
 1               5

<210> SEQ ID NO 28
<211> LENGTH: 5
<212> TYPE: PRT
<213> ORGANISM: Artificial Sequence
<220> FEATURE:
<221> NAME/KEY: VARIANT
<222> LOCATION: (1)...(1)
<223> OTHER INFORMATION: Xaa = Ser, Tyr, Cys, Trp, Thr, Asn, Lys or Arg
<223> OTHER INFORMATION: EGIII-like cellulase amino acid string
<221> NAME/KEY: VARIANT
<222> LOCATION: (2)...(2)
<223> OTHER INFORMATION: Xaa = Val or Pro
<221> NAME/KEY: VARIANT
<222> LOCATION: (3)...(3)
<223> OTHER INFORMATION: Xaa = Lys or Ala
<221> NAME/KEY: VARIANT
<222> LOCATION: (4)...(4)
<223> OTHER INFORMATION: Xaa = Ser or Ala
<221> NAME/KEY: VARIANT
<222> LOCATION: (5)...(5)
<223> OTHER INFORMATION: Xaa = Tyr or Phe

<400> SEQUENCE: 28

Xaa Xaa Xaa Xaa Xaa
 1               5

<210> SEQ ID NO 29
<211> LENGTH: 6
<212> TYPE: PRT
```

```
<213> ORGANISM: Artificial Sequence
<220> FEATURE:
<223> OTHER INFORMATION: EGIII-like cellulase amino acid string

<400> SEQUENCE: 29

Lys Asn Phe Phe Asn Tyr
 1               5

<210> SEQ ID NO 30
<211> LENGTH: 5
<212> TYPE: PRT
<213> ORGANISM: Artificial Sequence
<220> FEATURE:
<221> NAME/KEY: VARIANT
<222> LOCATION: (1)...(5)
<223> OTHER INFORMATION: Xaa = Asn or Gln
<223> OTHER INFORMATION: BOX1

<400> SEQUENCE: 30

Xaa Asn Leu Trp Gly
 1               5

<210> SEQ ID NO 31
<211> LENGTH: 14
<212> TYPE: DNA
<213> ORGANISM: Artificial Sequence
<220> FEATURE:
<221> NAME/KEY: misc_feature
<222> LOCATION: (1)...(14)
<223> OTHER INFORMATION: n = A,T,C or G
<223> OTHER INFORMATION: primer

<400> SEQUENCE: 31
aayaayytnt gggg                                                        14

<210> SEQ ID NO 32
<211> LENGTH: 14
<212> TYPE: DNA
<213> ORGANISM: Artificial Sequence
<220> FEATURE:
<221> NAME/KEY: misc_feature
<222> LOCATION: (1)...(14)
<223> OTHER INFORMATION: n = A,T,C or G
<223> OTHER INFORMATION: primer

<400> SEQUENCE: 32
caraayytnt gggg                                                        14

<210> SEQ ID NO 33
<211> LENGTH: 6
<212> TYPE: PRT
<213> ORGANISM: Artificial Sequence
<220> FEATURE:
<221> NAME/KEY: VARIANT
<222> LOCATION: (1)...(6)
<223> OTHER INFORMATION: Xaa = Phe, Leu, Tyr, Ile, Asn or Lys
<223> OTHER INFORMATION: BOX1'

<400> SEQUENCE: 33

Asn Asn Asn Xaa Trp Gly
 1               5

<210> SEQ ID NO 34
<211> LENGTH: 17
<212> TYPE: DNA
<213> ORGANISM: Artificial Sequence
<220> FEATURE:
<223> OTHER INFORMATION: primer
<221> NAME/KEY: misc_feature
```

```
<222> LOCATION: (1)...(17)
<223> OTHER INFORMATION: n = inosine

<400> SEQUENCE: 34
aayaayaayh wntgggg                                              17

<210> SEQ ID NO 35
<211> LENGTH: 5
<212> TYPE: PRT
<213> ORGANISM: Artificial Sequence
<220> FEATURE:
<223> OTHER INFORMATION: BOX2

<400> SEQUENCE: 35

Glu Leu Met Ile Trp
 1               5

<210> SEQ ID NO 36
<211> LENGTH: 15
<212> TYPE: DNA
<213> ORGANISM: Artificial Sequence
<220> FEATURE:
<221> NAME/KEY: misc_feature
<222> LOCATION: (1)...(15)
<223> OTHER INFORMATION: n = A,T,C or G
<223> OTHER INFORMATION: primer

<400> SEQUENCE: 36
garytnatga thtgg                                                15

<210> SEQ ID NO 37
<211> LENGTH: 15
<212> TYPE: DNA
<213> ORGANISM: Artificial Sequence
<220> FEATURE:
<221> NAME/KEY: misc_feature
<222> LOCATION: (1)...(15)
<223> OTHER INFORMATION: n = A,T,C or G
<223> OTHER INFORMATION: primer

<400> SEQUENCE: 37
ccadatcatn arytc                                                15

<210> SEQ ID NO 38
<211> LENGTH: 6
<212> TYPE: PRT
<213> ORGANISM: Artificial Sequence
<220> FEATURE:
<223> OTHER INFORMATION: BOX2'

<400> SEQUENCE: 38

Tyr Glu Leu Met Ile Trp
 1               5

<210> SEQ ID NO 39
<211> LENGTH: 18
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(18)
<223> OTHER INFORMATION: n = inosine

<400> SEQUENCE: 39
taygarytna tgathtgg                                             18
```

```
<210> SEQ ID NO 40
<211> LENGTH: 18
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(18)
<223> OTHER INFORMATION: n = inosine

<400> SEQUENCE: 40
ccadatcatn arytcrta                                              18

<210> SEQ ID NO 41
<211> LENGTH: 6
<212> TYPE: PRT
<213> ORGANISM: Artificial Sequence
<220> FEATURE:
<221> NAME/KEY: VARIANT
<222> LOCATION: (1)...(6)
<223> OTHER INFORMATION: Xaa = Pro or Cys
<223> OTHER INFORMATION: BOX3

<400> SEQUENCE: 41

Gly Thr Glu Xaa Phe Thr
 1               5

<210> SEQ ID NO 42
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<223> OTHER INFORMATION: primer

<400> SEQUENCE: 42
gtraanggyt crgtrcc                                               17

<210> SEQ ID NO 43
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<223> OTHER INFORMATION: primer

<400> SEQUENCE: 43
gtraanggyt crgtycc                                               17

<210> SEQ ID NO 44
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<223> OTHER INFORMATION: primer

<400> SEQUENCE: 44
gtraanggyt cygtrcc                                               17

<210> SEQ ID NO 45
<211> LENGTH: 17
<212> TYPE: DNA
```

```
<213> ORGANISM: Artificial Sequence
<220> FEATURE:
<221> NAME/KEY: misc_feature
<222> LOCATION: (1)...(17)
<223> OTHER INFORMATION: n = A,T,C or G
<223> OTHER INFORMATION: primer

<400> SEQUENCE: 45
gtraanggyt cygtycc                                              17

<210> SEQ ID NO 46
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<223> OTHER INFORMATION: primer

<400> SEQUENCE: 46
gtraarcayt cngtncc                                              17

<210> SEQ ID NO 47
<211> LENGTH: 27
<212> TYPE: DNA
<213> ORGANISM: Artificial Sequence
<220> FEATURE:
<223> OTHER INFORMATION: primer

<400> SEQUENCE: 47
ggaactctga actgcgcatg gtggacc                                   27

<210> SEQ ID NO 48
<211> LENGTH: 27
<212> TYPE: DNA
<213> ORGANISM: Artificial Sequence
<220> FEATURE:
<223> OTHER INFORMATION: primer

<400> SEQUENCE: 48
ggtccaggat gcgcagttca gagttcc                                   27

<210> SEQ ID NO 49
<211> LENGTH: 26
<212> TYPE: DNA
<213> ORGANISM: Artificial Sequence
<220> FEATURE:
<223> OTHER INFORMATION: primer

<400> SEQUENCE: 49
ccaactacag ctgtgatgtc aagaac                                    26

<210> SEQ ID NO 50
<211> LENGTH: 26
<212> TYPE: DNA
<213> ORGANISM: Artificial Sequence
<220> FEATURE:
<223> OTHER INFORMATION: primer

<400> SEQUENCE: 50
gttcttgaca tcacagctgt agttgg                                    26

<210> SEQ ID NO 51
<211> LENGTH: 32
<212> TYPE: DNA
<213> ORGANISM: Artificial Sequence
```

<220> FEATURE:
<223> OTHER INFORMATION: primer

<400> SEQUENCE: 51
ccaatttggt accgagtgct tcacgggcag tg                32

<210> SEQ ID NO 52
<211> LENGTH: 32
<212> TYPE: DNA
<213> ORGANISM: Artificial Sequence
<220> FEATURE:
<223> OTHER INFORMATION: primer

<400> SEQUENCE: 52
cactgcccgt gaagcactcg gtaccaaatt gg                32

<210> SEQ ID NO 53
<211> LENGTH: 26
<212> TYPE: DNA
<213> ORGANISM: Artificial Sequence
<220> FEATURE:
<223> OTHER INFORMATION: primer

<400> SEQUENCE: 53
ccaggttcac ggtcagggac ttcagg                      26

<210> SEQ ID NO 54
<211> LENGTH: 26
<212> TYPE: DNA
<213> ORGANISM: Artificial Sequence
<220> FEATURE:
<223> OTHER INFORMATION: primer

<400> SEQUENCE: 54
cctgaagtcc ctgaccgtga acctgg                      26

<210> SEQ ID NO 55
<211> LENGTH: 27
<212> TYPE: DNA
<213> ORGANISM: Artificial Sequence
<220> FEATURE:
<223> OTHER INFORMATION: primer

<400> SEQUENCE: 55
cgtgacttca gcggtgacat caaggac                     27

<210> SEQ ID NO 56
<211> LENGTH: 27
<212> TYPE: DNA
<213> ORGANISM: Artificial Sequence
<220> FEATURE:
<223> OTHER INFORMATION: primer

<400> SEQUENCE: 56
gtccttgatg tcaccgctga agtcacg                     27

<210> SEQ ID NO 57
<211> LENGTH: 28
<212> TYPE: DNA
<213> ORGANISM: Artificial Sequence
<220> FEATURE:
<223> OTHER INFORMATION: primer

<400> SEQUENCE: 57
gtcggaacag agtccttcac aggcggtc                    28

<210> SEQ ID NO 58
<211> LENGTH: 28
<212> TYPE: DNA
<213> ORGANISM: Artificial Sequence
<220> FEATURE:
<223> OTHER INFORMATION: primer

<400> SEQUENCE: 58
gaccgcctgt gaaggactct gttccgac                                28

<210> SEQ ID NO 59
<211> LENGTH: 28
<212> TYPE: DNA
<213> ORGANISM: Artificial Sequence
<220> FEATURE:
<223> OTHER INFORMATION: primer

<400> SEQUENCE: 59
gtcggaacag agcccttcac aggcggtc                                28

<210> SEQ ID NO 60
<211> LENGTH: 28
<212> TYPE: DNA
<213> ORGANISM: Artificial Sequence
<220> FEATURE:
<223> OTHER INFORMATION: primer

<400> SEQUENCE: 60
gaccgcctgt gaagggctct gttccgac                                28

<210> SEQ ID NO 61
<211> LENGTH: 26
<212> TYPE: DNA
<213> ORGANISM: Artificial Sequence
<220> FEATURE:
<223> OTHER INFORMATION: primer

<400> SEQUENCE: 61
ccaggttcac gagcagggac ttcagg                                  26

<210> SEQ ID NO 62
<211> LENGTH: 26
<212> TYPE: DNA
<213> ORGANISM: Artificial Sequence
<220> FEATURE:
<223> OTHER INFORMATION: primer

<400> SEQUENCE: 62
cctgaagtcc ctgctcgtga acctgg                                  26

<210> SEQ ID NO 63
<211> LENGTH: 27
<212> TYPE: DNA
<213> ORGANISM: Artificial Sequence
<220> FEATURE:
<223> OTHER INFORMATION: primer

<400> SEQUENCE: 63
cgtgacttca gcagtgacat caaggac                                 27

<210> SEQ ID NO 64
<211> LENGTH: 27
<212> TYPE: DNA
<213> ORGANISM: Artificial Sequence -continued

```
<220> FEATURE:
<223> OTHER INFORMATION: primer

<400> SEQUENCE: 64
gtccttgatg tcactgctga agtcacg                                        27
```